(12) United States Patent
Broly et al.

(10) Patent No.: US 8,784,812 B2
(45) Date of Patent: Jul. 22, 2014

(54) METHODS FOR TREATING AUTOIMMUNE DISEASES USING A TACI-IG FUSION MOLECULE

(75) Inventors: Herve Broly, Saint Selve (FR); Jennifer Visich, Seattle, WA (US); Ivan Nestorov, Issaquah, WA (US); Sharon Busby, Seattle, WA (US); Jane Gross, Seattle, WA (US)

(73) Assignees: Zymogenetics, Inc., Seattle, WA (US); Ares Trading S.A., Aubonne (CH)

( * ) Notice: Subject to any disclaimer, the term of this patent is extended or adjusted under 35 U.S.C. 154(b) by 439 days.

(21) Appl. No.: 11/748,978

(22) Filed: May 15, 2007

(65) Prior Publication Data

US 2007/0274984 A1 Nov. 29, 2007

Related U.S. Application Data

(60) Provisional application No. 60/747,270, filed on May 15, 2006.

(51) Int. Cl.
*A61K 39/395* (2006.01)
*A61K 31/00* (2006.01)

(52) U.S. Cl.
USPC ........................... 424/134.1; 514/1.1; 514/7.9

(58) Field of Classification Search
None
See application file for complete search history.

(56) References Cited

U.S. PATENT DOCUMENTS

| | | | |
|---|---|---|---|
| 4,331,647 A | 5/1982 | Goldenberg | |
| 4,486,533 A | 12/1984 | Lambowitz | |
| 4,579,821 A | 4/1986 | Palmiter et al. | |
| 4,599,311 A | 7/1986 | Kawasaki | |
| 4,601,978 A | 7/1986 | Karin | |
| 4,615,974 A | 10/1986 | Kingsman et al. | |
| 4,656,134 A | 4/1987 | Ringold | |
| 4,661,454 A | 4/1987 | Botstein et al. | |
| 4,713,339 A | 12/1987 | Levinson et al. | |
| 4,784,950 A | 11/1988 | Hagen et al. | |
| 4,845,075 A | 7/1989 | Murray et al. | |
| 4,870,008 A | 9/1989 | Brake | |
| 4,882,279 A | 11/1989 | Cregg | |
| 4,931,373 A | 6/1990 | Kawasaki et al. | |
| 4,935,349 A | 6/1990 | McKnight et al. | |
| 4,946,778 A | 8/1990 | Ladner et al. | |
| 4,956,288 A | 9/1990 | Barsoum | |
| 4,977,092 A | 12/1990 | Bitter | |
| 4,990,446 A | 2/1991 | Oberto et al. | |
| 5,037,743 A | 8/1991 | Welch et al. | |
| 5,063,154 A | 11/1991 | Fink et al. | |
| 5,139,936 A | 8/1992 | Botstein et al. | |
| 5,143,830 A | 9/1992 | Holland et al. | |
| 5,155,027 A | 10/1992 | Sledziewski et al. | |
| 5,162,222 A | 11/1992 | Guarino et al. | |
| 5,162,228 A | 11/1992 | Sumino et al. | |
| 5,208,146 A | 5/1993 | Irie | |
| 5,223,409 A | 6/1993 | Ladner et al. | |
| 5,403,484 A | 4/1995 | Ladner et al. | |
| 5,523,227 A | 6/1996 | Bram et al. | |
| 5,541,291 A | 7/1996 | Keene | |
| 5,567,584 A | 10/1996 | Sledziewski et al. | |
| 5,571,698 A | 11/1996 | Ladner et al. | |
| 5,595,721 A | 1/1997 | Kaminski et al. | |
| 5,637,677 A | 6/1997 | Greene et al. | |
| 5,650,550 A | 7/1997 | Korach et al. | |
| 5,693,762 A | 12/1997 | Queen et al. | |
| 5,716,808 A | 2/1998 | Ramond | |
| 5,736,383 A | 4/1998 | Raymond | |
| 5,739,277 A | 4/1998 | Presta et al. | |
| 5,969,102 A | 10/1999 | Bram et al. | |
| 6,015,801 A | 1/2000 | Daifoitis et al. | |
| 6,316,222 B1 | 11/2001 | Bram et al. | |
| 6,500,428 B1 | 12/2002 | Bram et al. | |
| 6,537,540 B1 * | 3/2003 | Burstein et al. | ............. 424/93.2 |
| 6,716,576 B1 | 4/2004 | Yu et al. | |
| 6,774,106 B2 | 8/2004 | Theill et al. | |
| 7,501,487 B1 | 3/2009 | Mangelsdorf et al. | |
| 2003/0022233 A1 | 1/2003 | Goodwin | |
| 2003/0103986 A1 | 6/2003 | Rixon et al. | |
| 2004/0013674 A1 | 1/2004 | Ambrose et al. | |
| 2005/0070689 A1 | 3/2005 | Dixit et al. | |
| 2005/0163775 A1 | 7/2005 | Chan et al. | |
| 2005/0183148 A1 | 8/2005 | Bram et al. | |
| 2006/0034852 A1 | 2/2006 | Rixon et al. | |
| 2006/0067933 A1 | 3/2006 | Gross et al. | |
| 2006/0073146 A1 | 4/2006 | Ashkenazi et al. | |
| 2006/0286093 A1 | 12/2006 | Gross et al. | |

(Continued)

FOREIGN PATENT DOCUMENTS

AU 2006201471 A1 5/2006
EP 0 869 180 A1 10/1998

(Continued)

OTHER PUBLICATIONS

Wang et al, (Nature Immunology, 2(7):632-637, Jul. 2001).*
Martino, FierceBiotech, pp. 1-4. Nov. 9, 2006 Zymogenics and Serono to Begin TACI-IG Cinical Studies in B-Cell Malignancies, first reported Business Wire—Oct 4, 2004.*
Takashi et al (Japanese journal of Science, 28(5):333-42, Oct. 2005; abstract only).*
Stohl, W., Endoc. Metal. Imune Disord. Drug Targets, Dec. 1, 2006, 6/4, 351, abstract only.*
Wang et al (Nature Immunology 2(7):632-637, 2001).*
Bodmer, et al., "The Molecular Architecture of the TNF Superfamily." Trends in Biochemical Sciences, vol. 27, No. 1, pp. 19-24 (Jan. 2002).
Cheema, et al., "Elevated Serum B Lymphocyte Stimulator Levels in Patients with Systemic Immune-Based Rheumatic Diseases," Arthritis & Rheumatism, vol. 44, No. 6, pp. 1313-1319 (Jun. 6, 2001).

(Continued)

*Primary Examiner* — Patricia A Duffy
(74) *Attorney, Agent, or Firm* — Morgan, Lewis & Bockius LLP

(57) ABSTRACT

In various embodiments, the present invention provides methods and compositions for treatment of autoimmune diseases, including rheumatoid arthritis, for example comprising administering to a patient in need of such treatment a TACI-Ig fusion molecule. In one embodiment, the TACI-Ig fusion molecule is administered in amount sufficient to slow, suppress or inhibit proliferation-inducing functions of BlyS and APRIL.

17 Claims, 2 Drawing Sheets

(56) References Cited

U.S. PATENT DOCUMENTS

| | | |
|---|---|---|
| 2007/0071760 A1 | 3/2007 | Broly et al. |
| 2007/0264689 A1 | 11/2007 | Gross et al. |
| 2007/0269443 A1* | 11/2007 | Kalled et al. ............... 424/153.1 |

FOREIGN PATENT DOCUMENTS

| | | |
|---|---|---|
| EP | 1666052 A1 | 6/2006 |
| GB | 9828628.9 | 12/1998 |
| WO | WO 91/11465 | 8/1991 |
| WO | WO 94/06463 | 3/1994 |
| WO | WO 94/09137 | 4/1994 |
| WO | WO 95/35501 | 12/1995 |
| WO | WO 96/18641 | 6/1996 |
| WO | WO 96/27011 | 9/1996 |
| WO | WO 97/09137 | 3/1997 |
| WO | WO 97/17450 | 5/1997 |
| WO | WO 97/17451 | 5/1997 |
| WO | WO 97/33902 | 9/1997 |
| WO | WO 98/02536 | 1/1998 |
| WO | WO 98/02565 | 1/1998 |
| WO | WO 98/27114 | 6/1998 |
| WO | WO 98/18921 | 7/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | 99/12964 | 3/1999 |
| WO | WO 99/11791 | 3/1999 |
| WO | WO 99/12964 | 3/1999 |
| WO | WO 99/12965 | 3/1999 |
| WO | WO 00/03995 | 1/2000 |
| WO | 00/40714 | 7/2000 |
| WO | WO 00/39295 | 7/2000 |
| WO | WO 00/40716 | 7/2000 |
| WO | WO 00/43032 | 7/2000 |
| WO | WO 00/50597 | 8/2000 |
| WO | WO 00/62790 | 10/2000 |
| WO | WO 00/67034 | 11/2000 |
| WO | WO 01/12812 A2 | 2/2001 |
| WO | WO 01/24811 A1 | 4/2001 |
| WO | WO 01/60397 | 8/2001 |
| WO | WO 01/77342 | 10/2001 |
| WO | WO 01/81417 A2 | 11/2001 |
| WO | WO 01/87977 | 11/2001 |
| WO | PCT/JP01/06944 | 2/2002 |
| WO | WO 02/14504 | 2/2002 |
| WO | WO 02/38766 | 5/2002 |
| WO | WO 02/066516 A2 | 8/2002 |
| WO | WO 02/094852 A2 | 11/2002 |
| WO | WO 03/01877 | 1/2003 |
| WO | WO 03/014294 A2 | 2/2003 |
| WO | WO 03/55979 | 7/2003 |
| WO | 2003/097040 A1 | 11/2003 |
| WO | WO 2005/005462 A2 | 1/2005 |
| WO | WO 2005/042009 A1 | 5/2005 |
| WO | WO 06/52493 | 5/2006 |
| WO | WO 06/68867 | 6/2006 |
| WO | WO 07/19618 | 2/2007 |
| WO | WO 2007/019573 A2 | 2/2007 |
| WO | WO 2007/019575 A2 | 2/2007 |
| WO | WO 07/134326 | 11/2007 |

OTHER PUBLICATIONS

Cheson, et al., "National Cancer Institute-Sponsored Working Group Guidelines for Chronic Lymphocytic Leukemia: Revised Guidelines for Diagnosis and Treatment," Blood, vol. 87, No. 12, pp. 4990-4997 (Jun. 15, 1996).

Davidson and Diamond, "Autoimmune Diseases," N Engl J Med, vol. 345, No. 5, pp. 340-350 (Aug. 2, 2001).

Ding and Jones, "Belimumab Human Genome Sciences/Cambridge Antibody Technology," Current Opinion in Investigational Drugs, vol. 7, No. 5, pp. 464-472 (2006).

Eisen, "Aberrant Immune Responses," General Immunology, J.B. Lippincott Company, pp. 215-225 (1990).

Falk, et al., "The Systemic Amyloidoses," N Engl J Med, vol. 337, No. 13, pp. 898-909 (Sep. 25, 1997).

Feldmann, et al., "Evaluation of the Role of Cytokines in Autoimmune Disease: The Importance of TNFa in Rheumatoid Arthritis," Progress in Growth Factor Research, vol. 4, pp. 247-255 (1992).

Feldmann and Maini, "The Role of Cytokines in the Pathogenesis of Rheumatoid Arthritis," Rheumatology, vol. 38, Suppl. 2, pp. 3-7 (1999).

Ginzler, et al., "Safety Pharmacokinetic and Pharmacodynamic Results of a Phase 1 Single and Double Dose-Escalation Study of LymphoStat-B (Human Monoclonal Antibody to BLyS) in SLE Patients," American College of Rheumatology Abstract Supplement, pp. S377 (Oct. 26, 2003).

Gras, et al., "BCMAp: An Integral Membrane Protein in the Golgi Apparatus of Human Mature B Lymphocytes." International Immunology, vol. 7, No. 7, pp. 1093-1106 (Mar. 28, 1995).

Groom, et al., "Association of BAFF/BLyS Overexpression and Altered B Cell Differentation wth Sjogren's Syndrome," Journal of Clinical Investigation, vol. 109, No. 1, pp. 59-68 (Jan. 2002).

Gross, et al., "TACI and BCMA are Receptors for a TNF Homologue Implicated in B-Cell Autoimmune Disease," Nature, vol. 404, pp. 995-999 (Apr. 27, 2000).

Gross, et al., "TACI-Ig Neutralizes Molecules Critical for B Cell Development and Autoimmune Disease: Impaired B Cell Maturation in Mice Lacking BLyS," Immunity, vol. 15, pp. 289-302 (Aug. 2001).

Hahne, et al., "APRIL, a New Ligand of the Tumor Necrosis Facor Family, Stimulates Tumor Cell Growth," J. Exp. Med, vol. 188, No. 6. pp. 1185-1190 (Sep. 21, 1998).

Halpern et al., "Chronic Administration of Belimumab, a BLyS Antagonist, Decreases Tissue and Peripheral Blood B-Lymphocyte Populations in Cynomolgus Monkeys: Pharmacokinetic, Pharmacodynamic, and Toxicologic Effects," Toxicological Sciences, vol. 91, No. 2, pp. 586-599 (2006).

Huard, et al., "BAFF Production by Antigen-Presenting Cells Provides T Cell Co-Stimulation," International Immunology, vol. 16. No. 3, pp. 467-475 (2004).

Huard, et al., "T Cell Costimulation by the TNF Ligand BAFF," Journal of Immunology, vol. 167, pp. 6225-6231 (2001).

Hymowitz, et al., "Structures of APRIL-Receptor Complexes," Journal of Biological Chemistry, vol. 280, No. 8, pp. 7218-7227 (2005).

Laabi, et al., "A New Gene, BCM, on Chromosome 16 is Fused to the Interleukin 2 Gene by a t(4;16) (q26;p13) Translocation in a Malignant T Cell Lymphoma," EMBO Journal, vol. 11, No. 11, pp. 3897-3904 (1992).

Laabi, et al., "The BCMA Gene, Preferentially Expressed During B Lymphoid Maturation, is Bidirectionally Transcribed," Nucleic Acids Research, vol. 22, No. 7, pp. 1147-1154 (1994).

MacKay, et al., "Mice Transgenic for BAFF Develop Lymphocytic Disorders Along with Autoimmune Manifestations," J. Exp. Med., vol. 190, No. 11, pp. 1697-1710 (Dec. 6, 1999).

Madry, "The Characterization of Murine BCMA Gene Defines it as a New Member of the Tumor Necrosis Factor Receptor Superfamily," International Immunology, vol. 10, No. 11, pp. 1693-1702 (Aug. 3, 1998).

Mariette, et al., "The Level of BLyS (BAFF) Correlates with the Titre of Autoantibodies in Human Sjogren's Syndrome," Ann Rheum Dis, vol. 62, pp. 168-171 (2003).

Marsters, et al., "Interaction of the TNF Homologues BLyS and APRIL with the TNF Receptor Homologues BCMA and TACI," Current Biology, vol. 10, No. 13, pp. 785-788 (Jun. 16, 2000).

Moon and Ryu, "TACI: Fc Scavenging B Cell Activating Factor (BAFF) Alleviates Ovalbumin-Induced Bronchial Asthma in Mice," Exp. Mol. Med., vol. 39, No. 3, pp. 343-352 (Jun. 2007).

Moore, et al., "BLyS: Member of the Tumor Necrosis Factor Family and B Lymphocyte Stimulator," Science, vol. 285, pp. 260-263 (Jul. 9, 1999).

Mukhopadhyay, et al., "Identification and Characterization of a Novel Cytokine, THANK, a TNF Homologue That Activates Apoptosis, Nuclear Factor-kB, and c-Jun NH2-Terminal Kinase," Journal of Biological Chemistry, vol. 274, No. 23, pp. 15978-15981 (1999).

(56) References Cited

OTHER PUBLICATIONS

Munafo, et al., "Safety, Pharmacokinetics and Pharmacodynamics of Atacicept in Healthy Volunteers," Eur J Clin Pharmacol, vol. 63, pp. 647-656 (Apr. 2, 2007).
Ng, et al., "B Cell-Activating Factor Belonging to the TNF Family (BAFF)-R is the Principal BAFF Receptor Facilitating BAFF Costimulation of Circulating T and B Cells," Journal of Immunology, vol. 173, pp. 807-817 (2004).
Panayi, "The Pathogenesis of Rheumatoid Arthritis: From Molecules to the Whole Patient," British Journal of Rheumatology, vol. 32, pp. 533-536 (1993).
Patel, et al., "Engineering an APRIL-specific B Cell Maturation Antigen," Journal of Biological Chemistry, vol. 279, No. 16, pp. 16727-16735 (Apr. 16, 2004).
Ramakrishnan and Scheid, "Diagnosis and Management of Acute Pyelonephritis in Adults," American Family Physician, vol. 71, No. 5, pp. 933-942 (Mar. 1, 2005).
Roschke, et al., "BLyS and APRIL Form Biologically Active Heterotrimers That are Expressed in Patients with Systemic Immune-Based Rheumatic Diseases," Journal of Immunology, vol. 169, pp. 4314-4321 (2002).
Schneider, "BAFF, a Novel Ligand of the Tumor Necrosis Factor Family, Stimulates B Cell Growth," J. Exp. Med, vol. 189, No. 11, pp. 1747-1756 (Jun. 7, 1999).
Thompson, et al., "BAFF Binds to the Tumor Necrosis Factor Receptor-like Molecule B Cell Maturation Antigen and is Important for Maintaining the Peripheral B Cell Population," J. Exp. Med., vol. 192, No. 1, pp. 129-135 (Jul. 3, 2000).
Thompson, et al., "BAFF-R, a Newly Identified TNF Receptor that Specifically Interacts with BAFF," Science, vol. 293, pp. 2108-2111 (Sep. 14, 2001).
Tsokos, "Lymphocytes, Cytokines, Inflammation, and Immune Trafficking," Current Opinion in Rheumatology, vol. 7, pp. 376-383 (1995).
Von Bulow and Bram, "NF-AT Activation Induced by a CAML-Interacting Member of the Tumor Necrosis Factor Receptor Superfamily," Science, vol. 278, pp. 138-141 (Oct. 3, 1997).
Wallach, "TNF Ligand and TNF/NGF Receptor Families," Dept of Biological Chemistry, Weizmann Institute of Science, pp. 377-411 (2000).
Xia et al., "TACI is a TRAF-Interacting Receptor for TALL-1, a Tumor Necrosis Factor Family Member Involved in B Cell Regulation," J. Exp. Med., vol. 192, No. 1, pp. 137-143 (Jul. 3, 2000).
International Search Report for WO 99/12964 dated Apr. 13, 1999.
International Search Report for WO 2007/019573 A3 dated Jun. 1, 2007.
International Search Report for WO 2007/019575 A3 dated May 9, 2007.
International Search Report of PCT/US2007/068982 dated Mar. 3, 2008.
Berenbaum, "Synergy, Additivism and Antagonism in Immunosuppression," Clin. Exp. Immunol., vol. 28, pp. 1-18 (1977).
Bilsborough, J., et al., "TACI-Ig Prevents the Development of Airway Hyper-Responsiveness in a Murine Model of Asthma," Clinical & Experimental Allergy, vol. 38, No. 12, pp. 1959-1968 (2008).
Dooley, M., et al., "Mycophenolate Mofetil Therapy in Lupus Nephritis: Clinical Observations," J. Am. Soc. Nephrol., vol. 10, pp. 833-839 (1999).
Jonsson., et al., "Mycophenolic Acid Inhibits Inosine 5'-Monophosphate Dehydrogenase and Suppresses Immunoglobulin and Cytokine Production of B Cells," International Immunopharmacology, vol. 3, pp. 31-37 (2003).
Koyama, et al., "Raised Serum APRIL Levels in Patients with Systemic Lupus Erythematosus," Ann Rheum. Dis., vol. 64, pp. 1065-1067 (2005).
Lee, H. J., "Protein Drug Oral Delivery: The Recent Progress," Arch. Pharm. Res., vol. 25, No. 5, pp. 572-584 (2002).
Pena-Rossi, C., et al., "An Exploratory Dose-Escalating Study Investigating the Safety, Tolerability, Pharmacokinetics and Pharmacodynamics of Intravenous Atacicept in Patients with Systemic Lupus Erythematosus," Lupus, vol. 18, No. 6, pp. 547-555 (2009).
Stein, et al., "APRIL Modulates B and T Cell Immunity," J. Clin. Invest., vol. 109, pp. 1587-1598 (2002).
Stohl, W., et al., "B Lymphocyte Stimulator Protein-Associated Increase in Circulating Autoantibody Levels May Require CD4+ T Cells: Lessons from HIV-Infected Patients," Clinical Immunology, vol. 104, No. 2, pp. 115-122 (2002).
Tak, P., et al., "Atacicept in Patients with Rheumatoid Arthirits: A, Multi-Center, double- Blind, Placebo-Controlled, Dose-Escalating, Single and Repeat Dose Study," Arthritis Rheum., vol. 58, No. 1, pp. 61-72 (2008).
U.S. Appl. No. 09/479,856 Restriction Requirement dated Jul. 28, 2000.
U.S. Appl. No. 09/569,245 Final office action dated Nov. 17, 2009.
U.S. Appl. No. 09/627,206 Final office action dated Oct. 27, 2009.
U.S. Appl. No. 11/502,134 Non-final office action dated Dec. 2, 2009.
U.S. Appl. No. 11/458,968 Notice of Allowance dated Dec. 16, 2009.
U.S. Appl. No. 12/057,133 Non-Final Office Action dated Feb. 4, 2010.
Jelinek, D., "Pathogenesis and Maintenance of Multiple Myeloma," Myeloma Today, vol. 6, No. 6, pp. 1-22 (2005).
Moreaux, J., et al., "BAFF and APRIL Protect Myeloma Cells From Apoptosis Induced by Interleukin 6 Deprivation and Dexamethasone," Blood, vol. 103, No. 8, pp. 3148-3157 (2004).
U.S. Appl. No. 11/501,999 Final Office Action dated Jun. 8, 2010.
U.S. Appl. No. 11/501,999 Non-final office action dated Dec. 4, 2009.
U.S. Appl. No. 11/502,134 Notice of Allowance dated Jul. 23, 2010.
U.S. Appl. No. 11/502,134 Final Office Action dated May 27, 2010.
U.S. Appl. No. 09/627,206 Advisory Action dated Mar. 25, 2010.
U.S. Appl. No. 09/627,206 Notice of Allowance dated Jul. 8, 2010.
U.S. Appl. No. 09/569,245 Advisory Action dated Mar. 11, 2010.
U.S. Appl. No. 12/057,133 Final Office Action dated Aug. 17, 2010.
U.S. Appl. No. 12/057,133 Examiner Interview Summary dated Jan. 27, 2011.
U.S. Appl. No. 12/952,048 Restriction requirement dated May 12, 2011.
Ansell, et al., Clin. Cancer Res., vol. 14, No. 4, pp. 1105-1110 (Feb. 15, 2008).
International Preliminary Report on Patentability of PCT/US2008/080177 dated Apr. 20, 2010.
Nestorov, I., et al., Pharmacokinetics and Biological Activity of Atacicept in Patients with Rheumatoid Arthritis, The Journal of Clinical Pharmacology, vol. 48, p. 406-417 (2008).
Rossi, J., et al., "Atacicept in Relapsed/Refractory Multiple Myeloma or Active Waldenstrom's Macroglobulinemia: A Phase I Study" British Journal of Cancer, vol. 101, pp. 1051-1058 (2009).
Tak, P. P., et al., "Atacicept in Patients with Rheumatoid Arthritis: Results of a Multicenter, Double- Blind, Placebo-Controlled, Dose-Escalating, Single- and Repeated-Dose Study," Arthritis Rheum., vol. 58, No. 1, pp. 61-72 (2008).
Anonymous, "Waldenstrom Macroglobulinemia," Wikipedia, The Free Encyclopedia, http://en.wikipedia.org/wiki/Waldenstrom's_macroglobulinemai.
Barlogie, B., et al. Extended Survival in Advanced and Refractory Multiple Myeloma After Single-Agent Thalidomide: Identification of Prognostic Factors in a Phase 2 Study of 169 Patients, Blood, vol. 98, No. 2, pp. 492-494 (2001).
Brenner, S., et al., "Errors in Genome Annotation," Trends in Genetics, vol. 15, pp. 132-133 (1999).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology 111:2129-2138 (Nov. 1990).
Do, R., "Attenuation of Apoptosis Underlies B Lymphocyte Stimulator Enhancement of Humoral Immune Response." J. Exp. Med., vol. 192, No. 7, pp. 953-964 (2000).

(56) References Cited

OTHER PUBLICATIONS

Ibragimova, G., et al., "Stability of the B-Sheet of the WW Domain: A Molecular Dynamics Simulation Study," Biophysical Journal, vol. 77, pp. 2192-2198 (1999).
Kelly, K., "APRIL/TRDL-1, a Tumor Necrosis Factor-Like Ligand, Stimulates Cell Death," Cancer Research, vol. 60, pp. 1021-1027 (2000).
Lazar et al., "Transforming Growth Factor alpha: Mutation of Aspartic Acid 47 and Leucine 48 Results in Different Biological Activities" Molecular and Cellular Biology 8(3) 1247-1252 (1988).
Lin et al., "Structure-Function Relationships in Glucagon: Properties of Highly Purified Des-His1, Monoiodo-, and [Des-Asn 28,Thr29](homoserine lactone27)-glucagon" Biochemistry USA 14:1559-1563 (1975).
Martino, FierceBiotech, Press Release: ZymoGenetics and Serono to Begin TACI-Ig Clinical Studies in B-cell Malignancies, pp. 1-4, Nov. 9, 2006.
Richardson, P., et al., "A Phase 2 Study of Bortezomib in Relapsed, Refractoroy Myeloma," N Engl J Med, vol. 348, No. 26, pp. 2609-2617 (2003).
Ramanujam, M. et al., "Mechanism of Action of Transmembrane Activator and Calcium Modulator Ligand Interactor-Ig in Murine Systemic Lupus Erythematosus," J. Immunol., vol. 173, 3524-3534 (2004).
Schwartz et al., "A Superactive Insulin: [B10-Aspartic acid] insulin (human)" Proc Natl Acad Sci USA 84:6408-6411 (1987).
Smith, T., et al., "The Challenges of Genome Sequene annotation or the devil is in the details," Nature Biotechnology, vol. 15, 1222-1223 (1997).
Stein, et al., "Immunologic Markers in the Differential Diagnosis of Non-Hodgkins Lymphomas," Journal of Cancer Research and Clinical Oncology, vol. 101, p. 29, Abstract (1981).
Strand V. et al., "Biologic Therapies in Rheumatology: Lessons Learned, Future Directions," Nat. Rev. Drug. Discov., vol. 6, No. 1, 75-92 (2007).
Suntharalingam G., et al., "Cytokine Storm in a Phase 1 Trial of the Anti-CD28 Monoclonal Antibody TGN1412," N. Engl. J. Med., vol. 355, 1018-1028 (2006).
Yan M., et al., "Activation and Accumulation of B Cells in TACI-Deficient Mice," Nat. Immunol., vol. 2, 638-643 (2001).
Non-Final Office Action Communication issued in U.S. Appl. No. 11/502,134, dated Sep. 27, 2007.
Final Office Action Communication issued in U.S. Appl. No. 11/502,134, dated Jul. 2, 2008.
Advisory Action Communication issued in U.S. Appl. No. 11/502,134, dated Dec. 16, 2008.
Non-Final Office Action Communication issued in U.S. Appl. No. 11/502,134, dated Mar. 12, 2009.
"Restriction Requirement" issued in U.S. Appl. No. 11/501,999, dated Feb. 13, 2008.
Non-Final Office Action Communication issued in U.S. Appl. No. 11/501,999, dated May 30, 2008.
Final Office Action Communication issued in U.S. Appl. No. 11/501,999, dated Jan. 7, 2009.
Altschul, et al., Bull Math. Bio., vol. 48, pp. 603-666 (1986).
Anolik, J.H., et al., "New Treatments for SLE: Cell-Depleting and Anti-Cytokine Therapies," Best Practice & Research Clinical Rheumatology, vol. 19, No. 5, pp. 859-878 (2005).
Aviv, H., et al., "Purificaton of Biologically Active Globin Messenger RNA by Chromatography on Oligothymidylic acid Cellulose," Proc. Natl. Acad. Sci., vol. 69, pp. 1408-1412 (1972).
Bairoch, A., "The Prosite Dictionary of Sites and Patterns in Proteins, Its Current Status," Nucleic Acids Research, vol. 21, No. 13, pp. 3097-3103 (1993).
Bell, E., "TNF-R Homologues in Autoimmune Disease," Immunology Today, vol. 21, No. 6, p. 253 (Jun. 1, 2000).
Bilsborough, J., et al., "TACI-Ig Prevents the Development of Airway Hyper-Responsiveness in a Murine Model of Asthma," pp. 1-34.
Biosis Database, [online], Biosciences Information Service, Philadelphia, PA (Sep. 2008). Carbonatto, Michela, et al., Nonclinical Safety, Pharmacokinetics, and Pharmacodynamics of Atacicept, Database Accession No. PRV200800586339, Toxicological Sciences, vol. 105, No. 1, pp. 200-210 (Sep. 2008).
Bird, et al., Science, vol. 242, p. 423 (1988).
Birren, et al., EMBL Database Report for Accession No. AC003958, Jan. 6, 1998 (XP-002072294).
Bonning, et al., J. Gen. Virol., vol. 75, pp. 1551-1556 (1994).
Bram, R.J. and G.R. Crabtree, "Calcium Signalling in T Cells Stimulated by a Cyclophilin B-Binding Protein," Nature, vol. 371, pp. 355-358 (Sep. 22, 1994).
Bram, R.J., et al., "Identification of the Immunophilins Capable of Mediating Inhibition of Signal Transduction by Cyclosporin A and FK506: Roles of Calcineurin Binding and Cellular Location," Molecular and Cellular Biology, vol. 13, No. 8, pp. 4760-4769 (Aug. 1993).
Carter, et al., Proc. Nat. Acad. Sci., vol. 89, p. 42875 (1992).
Chan, A., et al., "Rescue Therapy Anti-CD20 Treatment in Neuroimmunologic Breakthrough Disease," J. Neurol. vol. 254, pp. 1604-1606 (2007).
Chazenbalk, Rapport, J. Biol. Chem., vol. 270, pp. 1543-1549 (1995).
Chirgwin, et al., Biochemistry, vol. 18, pp. 52-94 (1979).
Ciccarone, et al., Focus, vol. 15, p. 80 (1993).
Claros, M.G., et al., Comput. Appl. Biosci., vol. 10, pp. 685-686 (1994).
Clipstone, N.A. And G.R. Crabtee, "Identification of Calcineurin as a Key Signalling Enzyme in T-lymphocyte Activation," Nature, vol. 357, pp. 695-697 (Jun. 25, 1992).
Corsaro, Pearson Somatic Cell Genetics, vol. 7, p. 603 (1981).
Cosman, Stem Cells, vol. 12, pp. 440-455 (1994).
Courtenay-Luck, et al., "Genetic Manipulation of Monoclonal Antibodies, Cambridge University Press article, Monoclonal Antibodies, Production, Engineering and Clinical Application," p. 166 (1995).
Crabtee and Clipstone, Annu. Rev. Biochem., vol. 63, pp. 1045-1083 (1994).
Cyster, Nature Immunol., vol. 1, pp. 9-10 (2000).
Dall'Era, M., et al., Atacicept Reduces B Lymphocytes and Immunoglobulin Levels in Patients with Sytsemic Lupus Erythematosus (SLE), pp. 1-35.
Database Accession No. 014836, "Tumor Necrosis Factor Receptor Superfamily Member 13B" (2007).
Database Accession No. P20333, "Tumor Necrosis Factor Receptor 2 Precursor," (1995).
DiLillo, D.J., et al., "Maintenance of Long-Lived Plasma Cells and Serological Memory Despite Mature and Memory B Cell Depletion during CD20 Immunotherapy in Mice," The Journal of Immunology, vol. 180, pp. 361-371 (2008).
Durfee, T., et al., Genes Dev., vol. 7, pp. 555-569 (1993).
Dynan, T., Nature, vol. 316, pp. 774-778 (1985).
Emmel, E.A., et al., "Cyclosporin A Specifically Inhibits Function of Nuclear Proteins Involved in T Cell Activation," Science, vol. 246, pp. 1617-1620 (Dec. 22, 1989).
European Search Report of EP 05020384.3 dated Apr. 27, 2007.
European Search Report of EP 03016020 dated Jul. 10, 2003.
European Search Report of EP 05018984 dated Jan. 25, 2006.
European Search Report of EP 05018985 dated Jan. 16, 2006.
European Supplementary & Partial Search Report of EP 02734478 dated Dec. 7, 2007.
Excoffon, K., et al., "The Role of the Extracellular Domain in the Biology of the Coxsackievirus and Adenovirus Receptor," Am. J. Respir. Cell. Mol. Biol., vol. 32, pp. 498-503 (2005).
Fiering, S., et al., "Single Cell Assay of a Transcription Factor Reveals a Threshold in Transcription Activated by Signals Emanating from the T-cell Antigen Receptor," Genes & Development, vol. 4, pp. 1823-1834 (1990).
Friedman, J. and I. Weissman, "Two Cytoplasmic Candidates for Immunophilin Action Are Revealed by Affinity for a New Cyclophilin: One in the Presence and One in the Absence of CsA," Cell, vol. 66, pp. 799-806 (Aug. 23, 1991).
Gao, X., et al., "Advanced Transgenic and Gene-Targeting Approaches," Neurochemical Research, vol. 24, No. 9, pp. 1181-1188 (1999).
Garnier, et al., Cytotechnol., vol. 15, pp. 145-155 (1994).

(56) References Cited

OTHER PUBLICATIONS

Gleeson, et al., J. Gen. Microbiol., vol. 132, pp. 3459-3465 (1986).
Graham, et al., J. Gen. Viol., vol. 36, pp. 59-72 (1977).
Graham, Van der EB, Virology, vol. 52, p. 456 (1973).
Grantham, et al., Nuc.Acids Res., vol. 8, pp. 1893-1912 (1980).
Green, et al., Nat. Genet, vol. 7, p. 13 (1994).
Grosjean, Fiers, Gene, vol. 18, pp. 199-209 (1982).
Grussenmeyer, et al., Proc. Natl. Acad. Sci., vol. 82, pp. 7952-7954 (1985).
Haas, et al., Cur. Biol., vol. 6, pp. 315-324 (1996).
Hatzoglou, et al., J. Immunol., vol. 165, pp. 1322-1330 (2000) (XP002324045).
Hawley-Nelson, et al., Focus, vol. 15, p. 73 (1993).
Herrscher, R.F., et al., "The Immunoglobulin Heavy-chain Matrix-Associating Regions are Bound by Bright α B Cell-Specific Trans-Activator That Describes a New DNA-Binding Protein Family," Genes & Development, vol. 9, pp. 30607-3082 (1995).
Hillier, et al., GenBank Report for Accession No. H47097, Aug. 16, 1995.
Hill-Perkins, Possee, J. Gen Virol., vol. 71, pp. 971-976 (1990).
Holloway, M.P. And R.J. Bram, "A Hydrophobic Domain of $Ca^{2+}$ Modulating Cyclophilin Ligand Modulates Calcium Influx Signaling in T Lymphocytes," The Journal of Biological Chemistry, vol. 271, No. 15, pp. 8549-8552 (1996).
Holloway, M.P. And R.J.Bram, "Co-localization of Calcium-modulating Cyclophilin Ligand with Intracellular Calcium Pools," Journal of Biological Chemistry, vol. 273, No. 26, pp. 16346-16350 (Jun. 26, 1992).
Holm, Nuc. Acids Res., vol. 14, pp. 3075-3087 (1986).
Hopp, Woods Proc. Nat. Acad. Sci., vol. 78, pp. 3824-3828 (1981).
Hoth, M. And R. Penner, Calcium Release-Activated Calcium Current in Rat Mast Cells, Journal of Physiology, vol. 465, pp. 359-386 (1993).
Houdebine, "Transgenic Animal Bioreactors," Transgenic Research, vol. 9, pp. 305-320 (2000).
Houdebine, L-M., 2002, Journal of Biotechnology, vol. 98, p. 145-160.
Hubbard, M.J., et al., vol. 28, pp. 1868-1874 (1989).
Idemura, J. Mol Biol., vol. 158, pp. 573-597 (1982).
Imboden, J.B., et al., "The Antigen Receptor on a Human T Cell Line Initiates Activation by Increasing Cytoplasmic Free Calcium" Journal of Immunology, vol. 134, No. 2, pp. 663-665 (Feb. 1985).
Inbar, et al., Proc. Natl. Acad. Sci., vol. 69, p. 2659 (1972).
InNEXUS Lead Candidate DXL625Outpeforms Rituxan in Additional Animal Studies, [Online] Retrieved from Scientific Blogging, XP-002515036, (2008, pp. 1-2, Presentation American Association for Cancer Research, San Diego, CA, 2008, pp. 1-14.
Interlocutory Decision in Opposition Proceedings of EP 00902354 dated Nov. 30, 2007.
International Preliminary Report on Patentability of PCT/US00/00396 dated Jun. 19, 2001.
International Preliminary Report on Patentability of PCT/US2006/031277 dated Aug. 9, 2005.
International Preliminary Report on Patentability of PCT/US2007/068982 dated Nov. 27, 2008.
International Preliminary Report on Patentability of PCT/US98/04270 dated Jan. 5, 1999.
International Search Report of PCT/US00/00396 dated Jul. 7, 2000.
International Search Report of PCT/US2008/080177 dated Feb. 26, 2009.
International Search Report of PCT/US98/04270 dated Aug. 21, 1998.
Jones, et al., Nature, vol. 321, p. 522 (1986).
Kalled, S.L., et al., "BAFF; B Cell Survival Factor and Emerging Therapeutic Target for Autoimmune Disorders," Expert Opin. Ther. Targets, vol. 7, No. 1, pp. 115-123 (2003).
Karttunen, J., and N. Shastri, "Measurement of Ligand-induced Activation in Single Viable T Cells Using the lacZ Reporter Gene," Proc. Natl. Acad. Sci. USA, vol. 88, pp. 3972-3976 (May 1991).

Khare, et al., Proc. Natl. Acad. Sci. USA, vol. 97, pp. 3370-3375 (2000).
Kohler, et al., Nature, vol. 257, p. 495 (1975).
Kolb, et al., Insertion of a Foreign Gene into the Beta-casein Locus by Cre-mediated Site-specific Recombination, Gene, vol. 227, pp. 21-31 (1999).
Korganow, et al., Immunity, vol. 10, pp. 451-461 (1999).
Kyte, Doolittle, J. Mol. Biol., vol. 157, pp. 105-142 (1982).
Larrick, et al., Methods: A Companion to Methods in Enzymology, vol. 2, p. 106 (1991).
Leiter, E.H. & Lee, C-H., "Is There Evidence for Genetic Overlap Between Type 1 and Type 2 Diabestes?" Diabetes, vol. 54, Supp. 2, pp. S151-S158 (2005).
Leiter, et al. "Mice with targeted gene disruptions or gene insertions for diabetes research; problems, pitfalls, and potential solutions," Diabetologia, vol. 45, pp. 296-308 (2002).
Liapakis, G., et al., "Identification of Ligand Binding Determinants in the Somatostatin Receptor Subtypes 2 and 2," Journal of Biological Chemnistry, vol. 271, No. 34, pp. 20331-20339 (1996).
Lin, J.C., et al., "A Microdomain Formed by the Extracellular Ends of the Transmembrane Domains Promotes Activation of the G Protein-Coupled α-Factor Receptor," Molecular and Cellular Biology, vol. 24, No. 5, pp. 2041-2051 (2004).
Liu, J., et al., "Calcineurin is a Common Target of Cyclophilin-Cyclosporin A FKBP-FK506 Complexes," Cell, vol. 66, pp. 807-815 (Aug. 13, 1991).
Lonberg, et al., Nature, vol. 368, p. 856 (1994).
Losman, et al., Int. J. Cancer, vol. 46, p. 310 (1990).
Luckow, et al., J. Virol., vol. 67, pp. 4566-4579 (1993).
Mathey-Prevot, et al., Mol. Cell. Biol., vol. 6, pp. 4133-4135 (1986).
Merck, 17th Edition, Section 6-Pulmonary Disorders, pp. 568-569.
Miller, et al., GenBank Report for Accession No. R24371, Apr. 20, 1995.
Mishra, GenBank Report for Accession No. V64412, Mar. 1, 1999.
Neumann, et al., Embo J., vol. 1, pp. 841-845 (1982).
Nilsson, et al., Embo J., vol. 4, p. 1075, (1985).
Nilsson, et al., Methods Enzymol., vol. 198, p. 3 (1991).
Nisonoff, et al., Biochem. Biophys, vol. 89, p. 230 (1960).
Novake, Anne, J., et al., Blood, vol. 103, No. 2, pp. 689-694 (2004).
O'Keefe, S.J., et al., "FK-506 and CsA-sensitive Activation of the Interleukin-2 Promoter by Calcineurin," Nature, vol. 357, pp. 692-694 (Jun. 25, 1992).
Orlandi, et al., Proc. Natl. Acad. Sci., vol. 86, p. 3833 (1989).
Pack, et al., Bio/Technology, vol. 11, p. 1271 (1993).
Palacios, Steinemetz, Cell, vol. 41, pp. 727-734 (1985).
Pena-Rossi, C., et al., "An Exploratory Dose-Escalating Study Investigating the Safety, Tolerability, Pharmacokinetics and Pharmacodynamics of Intravenous Atacicept in Patients with Systemic Lupus Erythematosus," pp. 1-33.
Perez-Melgosa, et al., J. Immunol., vol. 163, p. 1123-27 (1999).
Porter, Biochem. J., vol. 73, p. 119 (1959).
Premack, B.A., et al., "Activation of $CA^{2+}$ Current in Jurkat T Cells Following the Depletion of $Ca^{2+}$ Stores by Microsomal $CA^{2+}$-ATPase Inhibitors," Journal of Immunology, vol. 152, pp. 5226-5240 (1994).
Putney, J.W., Jr., and G.St. J. Bird, The Signal for Capactiative Calcium Entry, Cell, vol. 75, pp. 199-201 (Oct. 22, 1993).
Ramser, et al., GenBank Report for Accession No. AL353996 (2000).
Raymond, et al., Yeast, vol. 14, pp. 11-23 (1998).
Roitt, I., et al., "Autoimmunity and Autoimmune Disease—27," Immunolgy, Fourth Edition, pp. 271-272 (1996).
Rudinger, J., "Characteristics of the Amino Acids as Components of Peptide Hormone Sequence," Peptide Hormones, University Park Press, Baltimore, pp. 1-7, (Jun. 1976).
Ryan, M., et al., "Antibody Targeting of B-Cell Maturaiton Antigen on Malignant Plasma Cells," Molecular Cancer Therapeutics, vol. 16, No. 11, US American Associate of Cancer Research pp. 3009-3018 (Nov. 2007).
Santee, S.M., and L.B. Owen-Schaub, "HumanTumor Necrosis Factor Receptor p75/80 (CD120B) Gene Structure and Promoter Characterization," The Journal of Biological Chemistry, vol. 271, No. 35, pp. 21151-21159 (1996).
Scatchard Ann. Ny. Acad. Sci., vol. 51, p. 660 (1949).

(56) References Cited

OTHER PUBLICATIONS

Sethi, S., et al., "Oxidized Omega-3 Fatty Acids in Fish Oil Inhibit Leukocyte-Endothelial Interactions Through Activation of Pparg," Blood, vol. 100, No. 4, pp. 1340-1346 (2002).
Shu, et al., J. Leukoc Biol., vol. 65, pp. 680-683 (1999).
Sigmund, C., Jun. 2000, Arterioscler. Thromb. Vasc. Biol., p. 1425-1429.
Silverman, G.J., et al., "B Cell Modulation in Rheumatology," Current Opinion in Pharmacology—Cancer/Immunomodulation 200708 GB, vol. 7, No. 4, pp. 426-433 (Aug. 4, 2007).
Singer, et al., J. Immun., vol. 150, p. 2844 (1993).
Sinkar, et al., J. Biosci., vol. 11, pp. 47-58 (1987).
Sipos, L., et al., Eur. J. Biochem., vol. 213, pp. 1333-1340 (1993).
Smith, et al., "The TNF Receptor Superfamily of Cellular and Viral Proteins" Activation, Costimulation and Death vol. 76, pp. 959-962 (1994).
Smith, Johnson, Gene. vol. 67, p. 31 (1988).
Stryer, L., "Flow of Genetic Information," Biochemistry Fourth Edicition, W.H. Freeman and Company, New York, pp. 111 (1996).
Stuve, O., et al., "Clinical Stabilization and Effective B-lymphocyte Depletion in the Cerebrospinal Fluid and Peripheral Blood of a Patient with Fulminant Relapsing-Remitting Multiple Sclerosis," Archives of Neurology, vol. 62, No. 10, pp. 1620-1623 (Oct. 2005).
Sulkowski, Trends in Biochem, vol. 1, p. 7 (1985).
Tak, P. P., et al., "Atacicept in Patients with Rheumatoid Arthirits: A, Multi-Center, double-Blind, Placebo-Controlled, Dose-Escalating, Single and Repeat Dose Study," pp. 1-36.
Takebe, Y., et al., Sr$\alpha$Promoter: an Efficient and Versatile Mammalian cDNA Expression System Composed of the Simian Virus 40 Early Prometer and the R-US Segment of Human T-Cell Leukemia Virus Type 1 Long Terminal Repeat, Molecular and Cellular Biology, vol. 8, No. pp. 466-472 (Jun. 1988).
Tashiro, K., et al., "Signal Sequence Trap: A Cloning Strategy for Secreted Proteins and Type I Membrane Proteins," Science, vol. 261, pp. 600-603 (Jul. 30, 1993).
Taylor, et al., Int. Immun., vol. 6, p. 579 (1994).
Truneh, A., et al., Early Steps of Lymphocyte Activation Bypassed by Synergy Between Calcium Ionophores and Phorbol Ester, Nature, vol. 313, pp. 318-320 (Jan. 24, 1985).
Tuan, et al., Connect Tiss. Res., vol. 34, pp. 1-9 (1996).
Varthakavi, Minocha, J. Gen. Virol., vol. 77, p. 1875 (1996).
Verweij, C.L., et al., "Cell Type Specificity and Activation Requirements for NFAT-1 (Nuclear Factor of Activated T-cells) Transcriptional Activity Determined by a New Method Using Transgenic Mice to Assay Transcriptional Activity of an Individual Nuclear Factor," Journal of Biological Chemistry, vol. 265, No. 26, pp. 15788-15795 (Sep. 15, 1990).
Von Bulow and R.J. Bram, "Activation of the Transcription Factor NFAT by a Novel CAML-Interacting Member of the Tumor Necrosis Factor Receptor Superfamily," Blood, vol. 90, No. 10, Suppl. 1, Part 1, pp. 246A-247 (1997).
Von Bulow, G.U., et al., "Molecular Cloning and Functional Characterization of Murine Transmembrane Activator and CAML Interactor (TACI) with Chromosomal Localization in Human and Mouse," Mammalian Genome, vol. 11, pp. 628-632 (2000).
Vugmeyster, Y., et al., "A Soluble BAFF Antagonist, BR3-Fc, Decreases Peripheral Blood B Cells and Lymphoid Tissue Marginal Zone and Follicular B Cells in Cynomolgus Monkeys," American Journal of Pathology 200602 US, vol. 168, No. 2, pp. 476-489 (Feb. 2, 2006).
Wada, A., et al., "Identification of Ligand Recognition Sites in Heat-Stable Enterotoxin Receptor, Membrane-Associated Guanylyl Cyclase C by Site-Directed Mutational Analysis," Infection and Immunity, vol. 64, No. 12, pp. 5144-5150 (1996).
Wain-Hobson, et al., Gene, vol. 13, pp. 355-364 (1981).
Ware, Nature, vol. 404, pp. 949-950 (2000).
Weiss, A., and D.R. Littman, et al., "Signal Transduction by Lymphocyte Antigen Receptors," Cell, vol. 76, pp. 263-274 (Jan. 28, 1994).
Wigler, et al., Cell, vol. 14, p. 7 25 (1978).
Wilson-Rawls, J., et al., Virology, vol. 201, pp. 66-76 (1994).
Wu, Y., et al., Tumor Necrosis Factor (TNF) Receptor Superfamily Member TACI is a High Affinity Receptor for TNF Family Members APRIL and BLyS, The Journal of Biological Chemistry, vol. 275, No. 45, pp. 35478-35485 (2000).
Yan, et al., Nature Immunol., vol. 1, pp. 37-41 (2000).
Yang, M., et al., "B Cell Maturation Antigen, the Receptor for a Proliferation-Inducing Ligand and B Cell-Activating Factor of the TNF Family, Induces Antigen Presentation in B Cells," Journal of Immunology, vol. 175, US The Williams and Wilkins Co., Baltimore, pp. 2814-2824 (Sep. 2005).
Yu, G., et al., "April and TALL-I and Receptors BCMA and TACI: System for Regulating Humoral Immunity," Nature, vol. 1, No. 3, pp. 252-256 (2000).
Zhou, et al., Blood, vol. 98, No. 11:808a, Abstract 3361 (2001).
Zhu, J., et al., "Plasma Cells and IL-4 in Chronic Bronchitis and Chronic Obstructive Pulmonary Disease," American Journal of Respiratory and Critical Care Medicine, vol. 175, US American Lung Association, New York, NY vol. 175, pp. 1125-1133 (Jun. 2007).
Zweifach, A., and R.S. Lewis, "Mitogen-regulated $CA^{2+}$ Current of T Lymphocytes is Activated by Depletion of Intracellular $CA^{2+}$ Stores," Proc. Natl. Acad. Sci. USA, vol. 90, pp. 6295-6299 (Jul. 1993).
U.S. Appl. No. 11/501,999 Final Office Action dated Jun. 12, 2009.
U.S. Appl. No. 11/501,999 Final office action dated Jan. 7, 2009.
U.S. Appl. No. 09/627,206 Restriction Requirement dated Sep. 7, 2001.
U.S. Appl. No. 09/627,206 Restriction Requirement dated Apr. 26, 2002.
U.S. Appl. No. 09/627,206 Non-final office action dated Aug. 8, 2002.
U.S. Appl. No. 09/627,206 Final Office Action dated Apr. 28, 2003.
U.S. Appl. No. 09/627,206 Advisory Action dated Mar. 3, 2004.
U.S. Appl. No. 09/627,206 Non-final Office action dated Aug. 6, 2004.
U.S. Appl. No. 09/627,206 Final Office action dated May 23, 2005.
U.S. Appl. No. 09/627,206 Non-final Office action dated Dec. 29, 2006.
U.S. Appl. No. 09/627,206 Non-final Office Action Dec. 7, 2007.
U.S. Appl. No. 09/627,206 Final Office Action dated Aug. 18, 2008.
U.S. Appl. No. 09/627,206 Non-final office action dated Feb. 11, 2009.
U.S. Appl. No. 11/200,992 Non-Final Office Action dated Mar. 21, 2008.
U.S. Appl. No. 11/200,992 Final Office Action dated Dec. 15, 2008.
U.S. Appl. No. 11/242,294 Non-Final office action dated Jun. 22, 2007.
U.S. Appl. No. 11/242,294 Final Office Action dated May 28, 2008.
U.S. Appl. No. 11/242,294 Notice of Allowance dated Oct. 24, 2008.
U.S. Appl. No. 12/057,133 Restriction Requirement dated Jul. 13, 2009.
U.S. Appl. No. 10/152,363 Restriction Requirement dated Oct. 31, 2003.
U.S. Appl. No. 10/152,363 Non-final office action dated Feb. 24, 2004.
U.S. Appl. No. 10/152,363 Final office action dated Apr. 1, 2005.
U.S. Appl. No. 09/569,245 Restriction Requirement dated Sep. 7, 2001.
U.S. Appl. No. 09/569,245 Restriction Requirement dated Apr. 10, 2002.
U.S. Appl. No. 09/569,245 Non-Final Office Action dated Aug. 8, 2002.
U.S. Appl. No. 09/569,245 Final Office Action dated Apr. 25, 2003.
U.S. Appl. No. 09/569,245 Advisory Action dated Mar. 9, 2004.
U.S. Appl. No. 09/569,245 Non-Final Office Action dated Aug. 6, 2004.
U.S. Appl. No. 09/569,245 Final office Action dated May 23, 2005.
U.S. Appl. No. 09/569,245 Non-Final Office Action dated Sep. 12, 2006.
U.S. Appl. No. 09/569,245 Non-Final Office Action dated Nov. 16, 2007.
U.S. Appl. No. 09/569,245 Final Office Ation dated Aug. 21, 2008.

(56) References Cited

OTHER PUBLICATIONS

U.S. Appl. No. 09/569,245 Non-Final Office Action dated Feb. 13, 2009.

U.S. Appl. No. 12/252,955 Restriction Requirement dated Sep. 4, 2009.

U.S. Appl. No. 12/359,801 Notice of Allowance dated Aug. 17, 2009.

U.S. Appl. No. 11/458,968 Restriction Requirement dated Mar. 23, 2009.

U.S. Appl. No. 11/458,968 Non-Final Office Action dated Jun. 24, 2009.

Ansel, Stephen M., et al., B-Lymphocyte Stimulator (BLyS) is Highly Expressed in Waldenstrom's Macroglobulinemia, Blood, (ASH Annual Meeting Abstracts), vol. 104, p. 917A, Abstract 2291 (2004).

Martineau, P., et al., "Expression of an Antibody Fragment at High Levels in the Bacterial Cytoplasm," J. Mol. Biol., vol. 280, pp. 117-127 (1998).

Santos, Daniel D., et al., "B-Lymphocyte Stimulator Protein (BLYS) is Expressed by Bone Marrow Mast and Lymphoplasmacytic Cells in Waldenstrom's Macroglobulinemia and Provides Signaling for Growth, Survival and IgM Secretion," Blood (ASH Annual Meeting Abstracts), vol. 104, p. 630A, Abstract 3358 (2004).

U.S. Appl. No. 12/952,048—Non-Final office action dated Sep. 23, 2011.

U.S. Appl. No. 12/952,048—Final office action dated Mar. 13, 2012.

U.S. Appl. No. 12/905,971 Non-final office action dated May 19, 2011.

U.S. Appl. No. 12/905,971 Final Office Action dated Oct. 17, 2011.

U.S. Appl. No. 11/501,999 Examiner's Answer dated Apr. 1, 2011.

\* cited by examiner

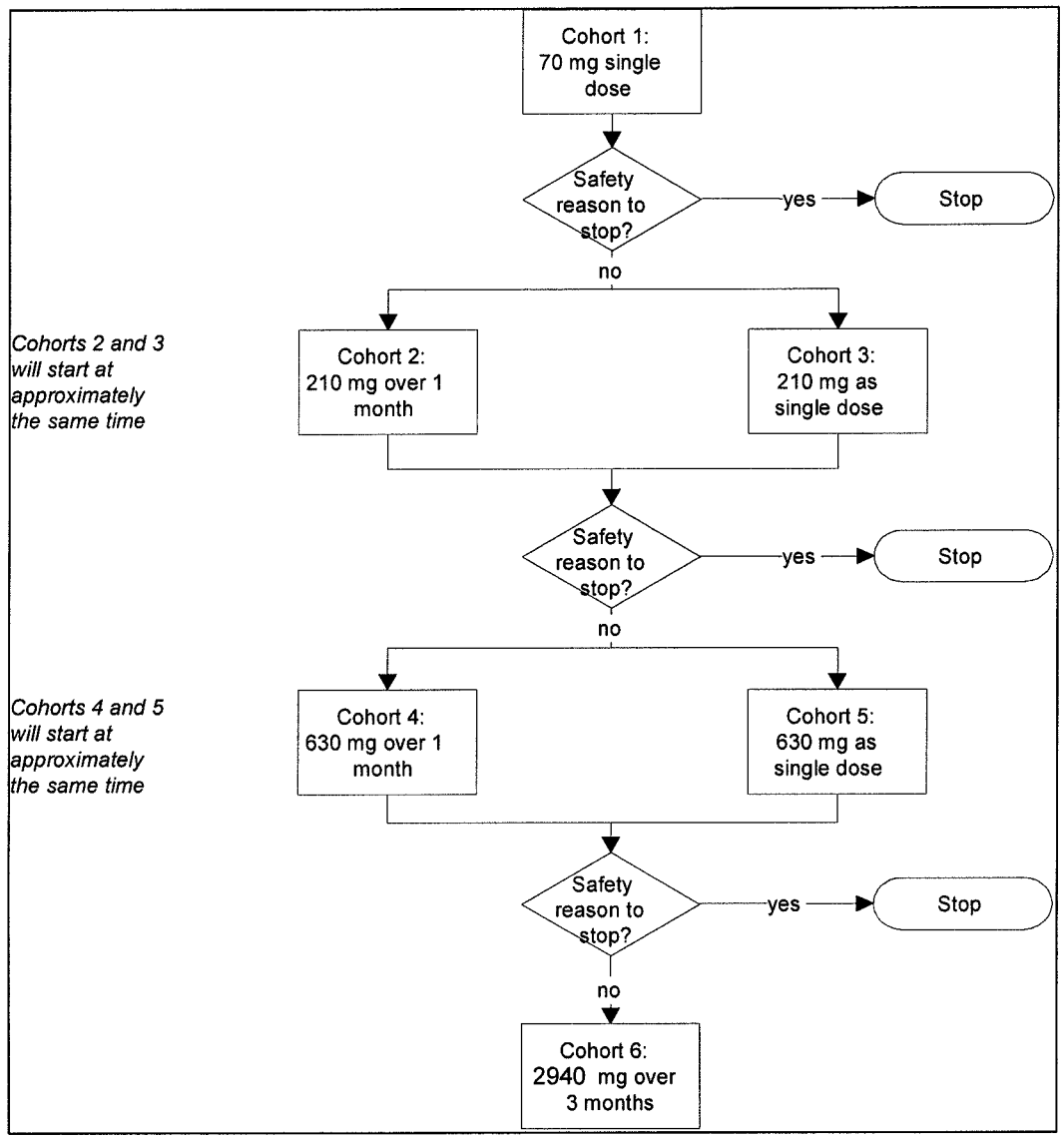
Figure 1. Dose Escalation Scheme.

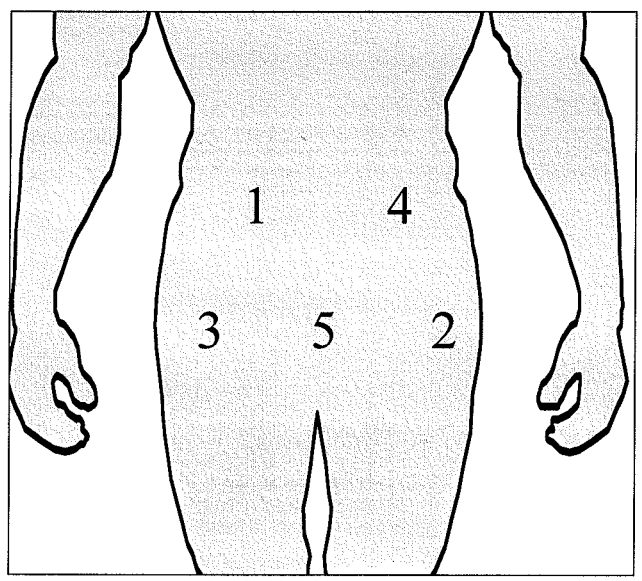
Figure 2. Areas for Subcutaneous Injection of TACI-Ig Molecule.

METHODS FOR TREATING AUTOIMMUNE DISEASES USING A TACI-IG FUSION MOLECULE

CROSS-REFERENCE TO RELATED APPLICATIONS

This application claims the benefit of U.S. Provisional Application No. 60/747,270, filed May 15, 2006, the contents of which is incorporated herein by reference.

FIELD OF THE INVENTION

In various embodiments, the present invention relates to methods and compositions for the treatment of autoimmune diseases or disorders of the immune system, comprising administering a TACI-Ig fusion protein which blocks functions of growth factors of the TNF family.

BACKGROUND OF THE INVENTION

The BlyS Ligand/Receptor Family

Three receptors, TACI (transmembrane activator or Calcium-Modulating Cyclophylin Ligand-interactor), BCMA (B-cell maturation antigen) and BAFF-R (receptor for B-cell activating factor, belonging to the TNF family), have been identified that have unique binding affinities for the two growth factors BlyS (B-lymphocyte stimulator) and APRIL (a proliferation-inducing ligand) (Marsters et al. Curr Biol 2000; 10(13): 785-788; Thompson et al. Science 2001; 293: 21 08-2111). TACI and BCMA bind both BLyS and APRIL, while BAFF-R appears capable of binding only BLyS with high affinity (Marsters et al. Curr Biol 2000; 10(13):785-788; Thompson et al. Science 2001; 293:21 08-2111.). As a result, BLyS is able to signal through all three receptors, while APRIL only appears capable of signaling through TACI and BCMA. In addition, circulating heterotrimer complexes of BLyS and APRIL (groupings of three proteins, containing one or two copies each of BLyS and APRIL) have been identified in serum samples taken from patients with systemic immune-based rheumatic diseases, and have been shown to induce B-cell proliferation in vitro (Roschke et al. J Immunol 2002; 169: 4314-4321). Amongst the Ig-fusion proteins for all three receptors, only TACI-Fc5 was able to block the biological activity of the heterotrimeric complexes (Roschke et al. J Immunol 2002; 169: 4314-4321).

BLyS and APRIL are potent stimulators of B-cell maturation, proliferation and survival (Gross et al. Nature 2000; 404: 995-999. Gross et al. Immunity 2001; 15(2): 289-302. Groom et al. J Clin Invest 2002; 109(1): 59-68). BLyS and APRIL may be necessary for persistence of autoimmune diseases, especially those involving B-cells. Transgenic mice engineered to express high levels of BLyS exhibit immune cell disorders and display symptoms similar to those seen in patients with Systemic Lupus Erythematosus (Cheson et al. Revised guidelines for diagnosis and treatment. Blood 1996; 87:4990-4997. Cheema et al. Arthritis Rheum 2001; 44(6): 1313-1319). Similarly, increased levels of BLyS/APRIL have been measured in serum samples taken from SLE patients and other patients with various autoimmune diseases like Rheumatoid Arthritis (Roschke et al. J Immunol 2002; 169:4314-4321; Mariette X., Ann Rheum Dis 2003; 62(2):168-171; Hahne et al. J Exp Med 1998; 188(6):1185-1190), extending the association of BLyS and/or APRIL and B-cell mediated diseases from animal models to humans.

Rheumatoid Arthritis

Rheumatoid Arthritis (RA) is a chronic inflammatory disease characterized by non-specific, usually symmetric inflammation of the peripheral joints, potentially resulting in progressive destruction of articular and periarticular structures. About 1% of the population is affected, women two to three times more often than men. Although the precise etiology of the disease is elusive, strong evidence suggests RA is an autoimmune disease. Several auto-antibodies are associated with RA including rheumatoid factor (RF) which is frequently associated with more severe disease, anti-nuclear factors and antibodies against native collagen type II and citrullinated peptides.

Prominent immunologic abnormalities that may be important in the pathogenesis of RA include immune complexes found in joint fluid cells and in vasculitis. Contributing to these complexes are antibodies (such as RF) produced by plasma cells and T helper cells that infiltrate the synovial tissue and which can produce pro-inflammatory cytokines. Macrophages and their cytokines (e.g. TNF, GMCS-F) are also abundant in diseased synovium. Increased levels of adhesion molecules contribute to inflammatory cell emigration and retention in the synovial tissue. Increased macrophage-derived lining cells are also prominent, along with some lymphocytes.

The role of T cells in the pathogenesis of RA is well established, while that of B cells is less well known. Nevertheless, B cells play many potential roles in the pathogenesis of RA, including acting as antigen-presenting cells, secreting pro-inflammatory cytokines, producing rheumatoid factor auto-antibody and activating T cells. The potential role of B cells is further supported by the positive results of clinical trials testing rituximab, a monoclonal antibody directed against CD20, in RA patients, most notably when given in combination with methotrexate or cyclophosphamide. These findings suggest that B cells are an appropriate target for therapeutic intervention in RA.

Established treatments of RA include disease modifying anti-rheumatic drugs (DMARD) such as hydroxychloroquine, sulfasalazine, methotrexate, leflunomide, rituximab, infliximab, azathioprine, D-penicillamine, Gold (oral or intramuscular), minocycline and cyclosporine, coritcosteroids such as prednisone and non-steroidal anti-inflammatory drugs (NSAIDS). These treatments are generally nonspecific, are frequently associated with serious side-effects and do not significantly affect the progression of joint destruction. Consequently, there is a long-felt need in the art to develop new methods for treating RA.

SUMMARY OF THE INVENTION

In various embodiments, the present invention is directed to methods of treating autoimmune diseases. Illustratively, the methods of the invention include administering to a patient a composition comprising a human immunoglobulin-constant domain and TACI extracellular domain or a fragment thereof which binds BlyS and/or APRIL.

In another embodiment, the invention comprises methods of treating autoimmune diseases, including RA, using a TACI-Ig fusion molecule that comprises the TACI extracellular domain or any fragment thereof that retains the ability to bind BlyS and/or APRIL.

In another embodiment, the invention comprises methods of treating RA comprising administering to a patient in need thereof, an effective amount of a fusion molecule comprising a human immunoglobulin-constant chain and TACI extracellular domain or a fragment of TACI extracellular domain that binds BlyS and/or APRIL. In one embodiment, the fragment of the extracellular domain of TACI comprises one or two cysteine repeat motifs. In another embodiment, the fragment is a fragment comprising amino acids 30-110 of the extracellular domain of TACI. In yet another embodiment, the fragment is a fragment comprising amino acids 1-154 of the extracellular domain of TACI (SEQ ID NO: 1).

In another embodiment, the invention comprises methods of treating RA by administering to a patient a composition comprising a fusion polypeptide, TACI-Fc5, comprising a human immunoglobulin-constant domain, Fc5, having the sequence set out as SEQ ID NO: 2 and a TACI extracellular domain having the sequence set out as SEQ ID NO: 1.

In still another embodiment, the invention comprises methods of treating RA by administering to a patient a composition comprising a fusion polypeptide comprising a human immunoglobulin-constant domain with the sequence set out as SEQ ID NO: 2 and a polypeptide which binds BlyS and/or APRIL and which is at least about 50%, at least about 60%, at least about 65%, at least about 70%, at least about 75%, at least about 80%, at least about 85%, at least about 90%, at least about 95% or at least about 99% identical to SEQ ID NO: 1.

Other autoimmune diseases can be treated by the methods of the invention by administering to a patient a fusion polypeptide comprising a human immunoglobulin-constant chain and TACI extracellular domain or a fragment of TACI extracellular domain that binds BlyS and/or APRIL. Such autoimmune diseases include, but are not limited to systemic lupus erythematosis (SLE), Graves disease, type I and type II diabetes, multiple sclerosis, Sjogren syndrome, scleroderma, glomerulonephritis, transplant rejection, e.g., organ and tissue allograft and xenograft rejection and graft versus host disease.

In one embodiment, the methods of the instant invention comprise administering to a RA patient a TACI-Ig fusion molecule in amounts from about 0.01 mg/kg of patient's body weight to about 10 mg/kg of patient's body weight. The TACI-Ig fusion molecule can be administered repeatedly at predetermined intervals. Illustratively, the molecule can be administered 7 or more times during a 12-week interval. This initial treatment with a TACI-Ig fusion polypeptide can be followed by administering the polypeptide on a bi-weekly (every other week) basis for at least 2 more additional weeks, for example the polypeptide can be administered on a bi-weekly basis for an additional 2 to 30 weeks. Alternately, the polypeptide may be administered on a weekly or daily basis.

According to the methods of the instant invention, a TACI-Ig fusion polypeptide can be administered to a RA patient subcutaneously, orally or intravenously and in combination with other medicaments. Such medicaments include, but are not limited to: DMARDs such as hydroxychloroquine, sulfasalazine, methotrexate, leflunomide, rituximab, infliximab, azathioprine, D-penicillamine, Gold (oral or intramuscular), minocycline and cyclosporine, coritcosteroids such as prednisone, NSAIDS, cytokines, anti-cytokines and interferons.

BRIEF DESCRIPTION OF THE FIGURES

FIG. 1. Dose-escalation decision tree for TACI-Fc5 treatment.

FIG. 2. Diagram of patient's body areas that can be used for subcutaneous injections of TACI-Ig molecule.

DETAILED DESCRIPTION OF THE INVENTION

In various embodiments, the instant invention pertains to methods of treating an autoimmune disease in a patient by inhibiting interaction of BlyS and/or APRIL with their receptors. The patient may be a mammal, for example a human. In one embodiment, the methods utilize an inhibitor that comprises: 1) a polypeptide that comprises a domain which is at least partially identical to TACI extracellular domain or a fragment thereof that binds BlyS and/or APRIL; and 2) a human immunoglobulin constant chain. In one embodiment, the methods of the invention utilize a fusion molecule comprising a human immunoglobulin constant chain and any polypeptide with at least about 50%, at least about 60%, at least about 65%, at least about 70%, at least about 75%, at least about 80%, at least about 85%, at least about 90%, at least about 95% or at least about 99% sequence identity to TACI extracellular domain. U.S. Pat. Nos. 5,969,102, 6,316,222 and 6,500,428 and U.S. patent application Ser. Nos. 09/569,245 and 09/627,206 (teachings of which are incorporated herein in their entirety by reference) disclose sequences for the extracellular domain of TACI as well as specific fragments of the TACI extracellular domain that interact with TACI ligands, including BlyS and APRIL. One illustrative fragment of the extracellular domain of TACI comprises one or two cysteine repeat motifs. Another illustrative fragment is a fragment comprising amino acids 30-110 of the extracellular domain of TACI or fragments thereof. Yet another illustrative fragment is a fragment comprising amino acids 1-154 of the extracellular domain of TACI (SEQ ID NO: 1) or fragments thereof.

Other fusion molecules useful for the methods of the invention include: a fusion polypeptide between a human immunoglobulin constant chain and the complete TACI extracellular domain or its ortholog or a fusion polypeptide between a human immunoglobulin constant chain and any fragment of the extracellular TACI domain that can bind BlyS and APRIL ligands. Any of the fusion molecules used in the methods of the invention can be referred to as a TACI-Ig fusion molecule.

TACI-Fc5 is one of the TACI-Ig fusion molecules useful for the methods of the invention. TACI-Fc5 is a recombinant fusion polypeptide comprising the extracellular, ligand-binding portion of receptor TACI from about amino acid 1 to about amino acid 154 (SEQ ID NO: 1) and the modified Fc portion of human IgG, Fc5 (SEQ ID NO: 2). Other TACI-Ig molecules useful for the methods of the instant invention include a fusion molecule comprising polypeptide with SEQ ID NO: 2 and a polypeptide which can bind BlyS and which is at least about 50%, at least about 60%, at least about 65%, at least about 70%, at least about 75%, at least about 80%, at least about 85%, at least about 90%, at least about 95% or at least about 99% identical to SEQ ID NO: 1.

Embodiments of the instant invention comprise methods of using a TACI-Ig fusion molecule for treating RA. Other autoimmune diseases that can be treated with the methods of the invention include systemic lupus erythematosis (SLE), Graves disease, type I and type II diabetes, multiple sclerosis, Sjogren syndrome, scleroderma, glomerulonephritis, transplant rejection, e.g., organ and tissue allograft and xenograft rejection, graft versus host disease or any other autoimmune disease that may be treated by decreasing the number of circulating mature B-cells and immunoglobulin-secreting cells and soluble immunoglobulins associated with such diseases.

Embodiments also comprise methods of treatment by administering to a patient a fusion molecule comprising a human immunoglobulin-constant domain and a polypeptide comprising any fragment of TACI extracellular domain that can bind BlyS and/or APRIL.

A TACI-Ig fusion molecule can be administered to a patient according to any suitable route of administration, including by not limited to orally, intravenously or subcutaneously.

TACI-Ig formulations useful for the methods of the invention can be prepared and stored as a frozen, sterile, isotonic solution. Such formulations can include other active ingredients and excipients such as, for example, sodium chloride, phosphate buffer and sodium hydroxide or O-phosphoric acid (pH 6.0). TACI-Ig formulations can be administered to a patient in combination with other medicaments. Such medicaments include, but are not limited to DMARDs such as hydroxychloroquine, sulfasalazine, methotrexate, leflunomide, rituximab, infliximab, azathioprine, D-penicillamine, Gold (oral or intramuscular), minocycline and cyclosporine, coritcosteroids such as prednisone, NSAIDS and drugs for the management of pain. Methods of the invention can be used in combination with other methods of treating autoimmune diseases. Such other methods of treatment include, but are not limited to surgery, acupuncture, physical therapy and gene therapy. TACI-Ig formulations can be administered prior, simultaneously or subsequently to other methods of treatment.

TACI-Fc5 has been shown to inhibit BLyS activation of B cell proliferation in vitro. Treatment of mice with TACI-Fc5 results in a partial block in B cell development that has a minimal effect on B cell precursors in the bone marrow and other cell lineages including peripheral blood T cells, monocytes and neutrophils. Transgenic mice engineered to overexpress a soluble form of the TACI receptor in the blood produce fewer mature B cells and show reduced levels of circulating antibody. The TACI-Fc5 transgenic mice had normal numbers of cells in the thymus, bone marrow and mesenteric lymph node. There were no significant differences in T cell populations in the thymus, lymph node and spleen. (Gross et al. Immunity 2001; 15(2): 289-302.)

Further, TACI-Ig can inhibit antigen-specific antibody production in an immune response in mice whether administered during the primary response or the secondary response to an antigen. In these studies, no effect on T cell response to ex vivo antigenic challenge was observed. In an animal model of systemic lupus erythematosus, treatment with TACI-Ig fusion proteins was effective in limiting the onset and progression of the disease. (Gross et al. Nature 2000; 404: 995-999). Similarly, in a mouse model of collagen-induced arthritis, TACI-Ig was able to inhibit the development of collagen-specific antibodies and reduce both the incidence of inflammation and the rate of occurrence of disease. (Gross et al. Immunity 2001; 15(2): 289-302).

A composition comprising a TACI-Ig fusion molecule may be administered to a patient once or may be administered to a patient repeatedly over a period of time. For example, a patient may receive one subcutaneous injection of TACI-Ig molecules after which his or her condition may be monitored. Patients who demonstrate improvement or at least stabilization of their condition may be administered a TACI-Ig fusion molecule repeatedly for an additional period of time. The additional period of time may be from about 2 to about 30 weeks. For example, a patient may be administered three doses of TACI-Ig fusion molecule during a four week interval. Alternately, a patient may be administered seven doses of a TACI-Ig fusion molecule during a twelve week interval. The administration of TACI-Ig molecules to a patient may be daily, bi-daily, weekly, bi-weekly, monthly, bimonthly, etc.

A TACI-Ig fusion molecule is administered to a patient in amount that is efficient for treating the patient's condition. In one embodiment, the term "treating" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. In another embodiment, the amount may range from 0.01 mg per 1 kg of patient's body weight to 10 mg per 1 kg of patient's body weight. An optimal dose for treating with a TACI-Ig fusion molecule can be developed by using a diagram of FIG. 1, described in further detail in Example 5.

A fusion TACI-Ig molecule may be delivered in any suitable manner. In one embodiment, the molecule is delivered by peritoneal injection. In another embodiment, the peritoneal injection is via subcutaneous injection. In another embodiment, the peritoneal injection is administered into the anterior abdominal wall. When more than one injection is required to administer a dose, the injections can be administered a few centimeters apart and relatively close together in time, for example as close as is reasonably possible. For repeated drug administration, the site of administration on the anterior abdominal wall can be rotated or alternated. Exemplary zones for subcutaneous injection into the anterior abdominal wall are depicted in FIG. 2 and include right upper external area, left lower external area, right lower external area, left upper external area, median lower area as well as right and left thighs and upper arms (FIG. 2). Alternatively, a TACI-Ig fusion molecule of the instant invention may delivered via intravenous injections or orally in a form of tablets, caplets, liquid compositions or gels, etc.

EXAMPLE 1

Testing TACI-Fc5 Pharmacology, Toxicology and Pharmacokinetics in an Experimental Animal Model TACI-Fc5 was evaluated in a host resistance model that provided the opportunity to directly assess the functional reserve of the immune system. Mice were challenged with influenza virus during TACI-Fc5 treatment. Dexamethasone, used as a positive control, resulted in an enhanced and prolonged viral infection. Administration of a single dose of TACI-Fc5 by the subcutaneous (SC) route reduced circulating B cells, total IgG and IgM, and influenza-specific IgG and IgM, but did not decrease the animals' ability to clear the viral infection.

Pivotal Safety Pharmacology studies showed that TACI-Fc5 induced no major changes of the nervous, respiratory and cardiovascular systems in mice or monkeys up to the SC dose of 80 mg/kg. Only in mice, a slightly increased hyper-alertness and locomotor activity, that may suggest minor and transient stimulant effect, was seen at 80 mg/kg, with a No-observed effect level (NOEL) equal to 20 mg/kg.

When administered to mice as a single dose by the intravenous (IV) or SC route, TACI-Fc5 did not induce mortality or appreciable general or local abnormal effects in the animals up to the highest technically feasible dose: 1200 mg/kg.

The administration to monkeys of TACI-Fc5 as a single dose by the SC route at the dose level of 240 mg/kg did not result in mortality or in any major toxic effects.

On the basis of the results obtained after 2 or 4 weeks of administration of TACI-Fc5 by subcutaneous route to mice at the doses of 5, 20 and 80 mg/kg/every second day, it may be concluded that the compound is well tolerated in this species at doses up to 80 mg/kg. Treatment-related modifications confined to the immune system were revealed at all doses.

These changes involved decreases in total and mature B cell numbers and IgG and IgM serum levels. Immunohistochemistry tests done in the spleen and lymph nodes confirmed depletion confined to B cells, with T cell number being unchanged. All these alterations, time- and dose-related in some cases, were considered as exaggerated pharmacological effects as expected in a responsive species after administration of very high doses of TACI-Fc5. Overall, these effects were seen after 2 and 4 weeks of treatment, without major indications of progression with time. They appeared to be almost completely reversible after 4 weeks of withdrawal of treatment, except for decreased B cell counts.

In order to ascertain B-cell modulation reversibility, a further study in mice was conducted at the doses of 5 and 20 mg/kg given for 4 weeks every 2nd day, with longer recovery periods. Recovery of total and mature circulating B cells was reached after two months of withdrawal at 5 mg/kg, and after 4 months at 20 mg/kg. Moreover, the injection induced a slight increase, compared to vehicle controls, of inflammatory changes at the injection sites at all doses.

Subcutaneous administration of TACI-Fc5 in monkeys did not induce major signs of toxicity at any of the doses tested: 5, 20 or 80 mg/kg/every 3rd day, when given for four consecutive weeks.

Local tolerability was considered satisfactory up to and including the highest dose tested. Dose-related and reversible slight or moderate changes of inflammatory origin (mainly perivascular mononuclear and eosinophilic cell infiltrates) were induced, but were considered mainly related to the local presence of exogenous proteins. Only at the high dose, a few animals showed slight or moderate subacute inflammation associated with a cyst formation in one of them.

Circulating B-cell number decreases at the lymphocyte subset determinations, as well as histological depletion of the spleen follicular marginal zone (known to be a B-cell dependent area) and decreases in total IgG and IgM serum levels were seen. They were considered a result of the pharmacodynamic properties of TACI-FcS, as shown by in vitro and in vivo pharmacology experiments. Their degree was exaggerated, as expected in toxicology studies in which animals are purposely administered high doses of the test compound. While low serum IgG and IgM levels and spleen lymphocytic depletion showed a clear tendency towards recovery within the one month withdrawal period allowed, total and mature circulating B cells did not show a similar behavior, indicating a longer time needed to recover.

At the end of the treatment period (week four), males and females of the high dose group (80 mg/kg) showed a slight but statistically significant decrease in mean total protein values compared to controls. A slight trend towards decrease was also seen at the same dose in week two, and at the end of the recovery period.

Serum protein modifications in the high dose females at the end of the dosing period included a decrease in globulin and increases in albumin percentage and alpha-1-globulin fraction. Alpha-1-globulin fraction also appeared higher than controls in group 3 females (20 mg/kg).

Immunogenicity of TACI-FcS was low in both mice (only a few females showed low levels of circulating binding antibodies during and after the treatment period) and monkeys (low levels were found after the recovery period in a few animals); there was no evidence of neutralizing antibodies in either species.

TACI-Fc5 was tested with the standard battery of in vivo tests to detect toxicology of reproduction and fertility (fertility test in male and female mice, treated by sc route at the doses of 5, 20 and 80 mg/kg/every 2nd day before and during the mating and up to the implantation period) and embryo-fetal development (embryo-fetal development study in female mice and rabbits, treated by sc route at the doses of 5, 20 and 80 mg/kg/every 2nd day during the organogenesis period).

The fertility test in mice showed a dose-related increase in pre- and post-implantation losses following exposure to 20 and 80 mg/kg/every 2nd day of TACI-Fc5 compared to the group.

Evaluation of the data obtained in mice of the embryo-fetal development study showed that no embryo-toxic effects were seen at any dose, and no compound-related fetal malformations were induced.

In rabbits, the embryo-fetal development study showed that treatment caused a dose-related lower body weight gain and lower food consumption in the pregnant animals treated with 20 or 80 mg/kg/every 2nd day. The above maternal changes were associated with an increased rate of resorptions and lower fetal body weight at the two higher doses.

These results suggest a possible effect of TACI-Fc5 on implantation of the mouse blastocyst in the uterus. The observed effects of TACI-Fc5 on maternal weight gain and food consumption were likely responsible for the observed effects on litter viability in rabbits exposed to 20 or 80 mg/kg/every 2nd day during organogenesis and that there is no direct toxicity of TACI-Fc5 on the fetus. No malformations were attributed to TACI-Fc5 treatment in these two animal species.

In addition, histological examination of male and female gonads and accessory sex organs was conducted in the 2-week and 1-month toxicity studies done by sc route in mice and monkeys in which TACI-Fc5 was administered every 2nd or every 3rd day, respectively, without evidence of treatment-related effects.

The local tolerance study in rabbits showed that TACI-Fc5 formulation was well tolerated locally when injected by the subcutaneous route to rabbits, at the dose of 70 mg/mL.

A single dose pharmacokinetic study in male mice by IV and SC routes was conducted in mice by either the intravenous route, at the dose of 1 mg/kg, or the subcutaneous route, at the doses of 1, 5 and 15 mg/kg.

Time to maximal absorption ($t_{max}$) was estimated between 4 hours to 16 hours, with a $t_{1/2}$ calculated to be around 40-50 hours.

An infusion-like profile was observed during the first 30 minutes after IV bolus administration, after which TACI-Fc5 was eliminated from the body with an elimination half-life of 44 hours. After subcutaneous administration, the ratio between the AUCs (Area Under the Curve) obtained at the 3 doses of 1, 5 and 15 mg/kg was 1:5:8 vs. the dose ratio of 1:5:15, suggesting a loss of dose-proportionality at the high dose.

TACI-Fc5's bioavailability by the subcutaneous route was of 76 and 89% at the doses of 1 and 5 mg/kg, but was lower than expected at 15 mg/kg (0, 42; calculated vs. the intravenous 1 mg/kg dose) in mice. Since the apparent elimination half-life was not altered, the lower bioavailability observed at the high dose could be explained by an increase of both clearance and volume of distribution or more probably by a decreased absorption due to the formation of a deposit at the site of injection.

A single dose pharmacokinetic study in male monkeys by IV and SC routes was conducted in male cynomolgus monkeys injected by either the intravenous route, at the dose of 1 mg/kg, or the subcutaneous route, at the doses of 1, 5 and 15 mg/kg.

Six male monkeys were divided into 2 groups of 3 animals each and received 2 administrations separated by a wash-out period of two weeks. Treatments of period 1 were 1 mg/kg IV (group 1) and 1 mg/kg SC (group 2) and treatments of period 2 were 5 mg/kg SC (group 1) and 15 mg/kg SC (group 2).

Time to maximal absorption ($t_{max}$) was estimated between 6 hours to 8 hours, with a $t_{1/2}$ calculated to be around 120-190 hours.

An infusion-like profile was observed in 2 out of 3 monkeys during the first 15 min after IV bolus administration, after which TACI-Fc5 was eliminated from the body with an elimination half-life of 179±29 hours. The volume of distribution at the steady state, Vss, was 382±82 mL/kg, a volume near the intracellular fluid volume.

After subcutaneous administration, the AUC vs. dose proportionality was good, i.e. 216, 1182 and 2732 h μg/mL for SC doses of 1, 5 and 15 mg/kg. The TACI-Fc5 bioavailability by the subcutaneous route (calculated vs. the 1 mg/kg IV dose) was 0.92, 1.02 and 0.77 at the low, intermediate and high doses. Therefore, TACI-Fc5 was almost completely absorbed by the subcutaneous route.

Low levels of TACI-Fc5 were found in the pre-dose samples for period 2 (between doses of 1 mg/kg by IV or SC routes, period 1, and doses of 5 or 15 mg/kg, respectively, in period 2) for all six monkeys, since during the 2-week washout period only 2 half-lives had elapsed, which was insufficient for a complete elimination of the administered compound (5 half-lives required). However, the AUC contribution of the previous dose could be estimated to represent only about 2% of the total AUC in period 2.

IgG serum levels showed a 10.2% decrease after IV dosing. The 15 mg/kg SC dose showed a slightly higher effect, while no differences were observed between the 1 and the 5 mg/kg SC doses (decreases of 8.6%, 8.4% and 12.3% after 1, 5 and 15 mg/kg doses respectively). IgM serum levels showed an 18.0% decrease after IV dosing. No differences were observed between the 3 SC doses (decreases of 23.5%, 23.0% and 24.2% after 1, 5 and 15 mg/kg doses respectively).

EXAMPLE 2

Determining TACI-Fc5 Tolerable Dose in Healthy Volunteers

The first phase I study of TACI-Fc5 is currently being completed. This is a double-blind, placebo controlled, dose escalating, sequential dose study investigating the safety, pharmacokinetics and pharmacodynamics of single doses of TACI-Fc5 administered subcutaneously to healthy male volunteers. An outline of the study design is presented below, along with summaries of the available data.

TACI-Fc5 was administered to healthy volunteers in a double-blind, placebo controlled, dose escalating, sequential dose study to investigate the safety, pharmacokinetics and pharmacodynamics single doses of TACI-Fc5 administered subcutaneously to healthy male volunteer.

Four groups of subjects were recruited. In each dosing group one subject was randomized to receive a placebo injection, with all others receiving TACI-Fc5. Following discharged from the investigational site at 24 hours post dose, subjects attended on an outpatient basis for seven weeks of scheduled assessments. Systemic and local tolerability of TACI-Fc5 were monitored by physical examination findings, injection site pain, local tolerability reactions at the site of injection(s) (redness, swelling, bruising and itching), vital signs, 12-lead ECGs (electrocardiogram), safety laboratory assessments and recording of adverse events.

Pharmacokinetic and pharmacodynamic markers were monitored throughout the seven-week period following dosing. The pharmacodynamic effect of TACI-Fc5 was monitored using a number of markers including: lymphocyte subsets by FACS analysis (plasma cells (CD138+), immature B cells (CD19+, IgD−), mature B cells (CD19+, IgD+), T-helper cells (CD5+, CD4+), cytotoxic T-cells (CD5+, CD8+), total T-cells (CD5+)), free BlyS, BlyS/TACI-Fc5 complex, IgG, IgM, anti-TACI-Fc5 antibodies.

Dose escalation was guided by an algorithm within the study protocol, based upon a review of data three weeks after dosing. Four groups were dosed: group 1 received 2.1 mg; group 2 received 70 mg; group 3 received 210 mg and group 4 received 630 mg.

Results: healthy male volunteers were administered single subcutaneous doses of TACI-Fc5 at doses ranging from 0.03 mg/kg to 9 mg/kg. Safety and tolerability data have been used, together with FACS analysis of lymphocyte subsets at week 3, to guide the dose escalation between cohorts. Four cohorts have been studied, as shown in Table 1.

TABLE 1

| Repartition of volunteers | | | |
|---|---|---|---|
| Cohort Number | Number of Subjects[c] | Dose Level | Administered Dose[a] |
| 1 | 6 | 0.03 mg/kg[b] | 2.1 mg |
| 2 | 6 | 1 mg/kg | 70 mg |
| 3 | 6 | 3 mg/kg | 210 mg |
| 4 | 5[d] | 9 mg/kg | 630 mg |

[a]At each dose level a nominal weight of 70 kg was assumed, with subjects receiving a standardized dose.
[b]Due to a dilution error the dose administered to cohort 1 was 10 fold lower than had been planned (0.3 mg/kg). This error was identified upon review of pharmacokinetic data from cohort 1, but following dosing of cohort 2.
[c]including 1 subject on placebo.
[d]One volunteer withdrew before the injection took place Demographic baseline characteristics were summarized for the population by cohort and overall and are shown in Table 2.

TABLE 2

| Demographic Characteristics | | | | | | | |
|---|---|---|---|---|---|---|---|
| Characteristic | Statistics | | Cohort 1 | Cohort 2 | Cohort 3 | Cohort 4 | Total |
| Age (years) | n | (SD) | 6 | 6 | 6 | 5 | 23 |
| | Mean | | 30.2 (7.0) | 33.0 (7.7) | 25.3 (6.8) | 35.0 (5.4) | 30.7 (7.4) |
| | Range | | 23-43 | 23-43 | 19-34 | 30-44 | 19-44 |
| Body Mass Index (kg/m2) | n | | 6 | 6 | 6 | 5 | 23 |
| | Mean | (SD) | 24.7 (1.7) | 26.0 (2.0) | 24.0 (3.5) | 25.3 (2.8) | 24.8 (2.4) |
| | Range | | 22.2-26.6 | 23.1-28.9 | 18.7-28 | 22.3-27.5 | 18.7-28.9 |
| Height (m) | n | | 6 | 6 | 6 | 5 | 23 |
| | Mean | (SD) | 1.82 (0.04) | 1.80 (0.08) | 1.77 (0.07) | 1.73 (0.06) | 1.78 (0.07) |
| | Range | | 1.77-1.88 | 1.71-1.91 | 1.67-1.85 | 1.68-1.78 | 1.67-1.91 |

TABLE 2-continued

Demographic Characteristics

| Characteristic | Statistics | | Cohort 1 | Cohort 2 | Cohort 3 | Cohort 4 | Total |
|---|---|---|---|---|---|---|---|
| Weight (kg) | n | | 6 | 6 | 6 | 5 | 23 |
| | Mean | (SD) | 81.7 (7.3) | 84.2 (12.1) | 74.7 (7.6) | 76.2 (9.2) | 79.0 (9.4) |
| | Range | | 71-91 | 69-101 | 67-84 | 63-89 | 63-101 |
| Sex n (%) | n | | 6 | 6 | 6 | 5 | 23 |
| | Male | | 6 (100%) | 6 (100%) | 6 (100%) | 5 (100%) | 23 (100%) |
| | Range | | 0 (0%) | 0 (0%) | 0 (0%) | 0 (0%) | 0 (0%) |
| Race n (%) | n | | 6 | 6 | 6 | 5 | 23 |
| | White | | 6 (100%) | 6 (100%) | 6 (100%) | 5 (100%) | 23 (100%) |
| | Other | | 0 (0%) | 0 (0%) | 0 (0%) | 0 (0%) | 0 (0%) |

Overall, mean + :SD age was 30.7+ 7.4 years and the mean body mass index was 24.8 kg/m2.
All volunteers were white males.

TACI-Fc5 was well tolerated in all groups. There were no apparent effects upon physical examination findings, vital signs or 12-lead ECGs.

TABLE 3

List of Treatment-Emergent Adverse Events Reported to Date

| Body System | Preferred Term | TACI-Fc5 2.1 mg N | TACI-Fc5 70 mg N | TACI-Fc5 210 mg N | TACI-Fc5 630 mg N | Placebo N | Total N | % |
|---|---|---|---|---|---|---|---|---|
| Eye Disorders | Eyelid Oedema | 1 | | | | | 1 | 2.1 |
| Gastrointestinal disorders | Abdominal pain upper | | | | | | 1 | 2.1 |
| | Diarrhoea | | 1 | 1 | 1 | 1 | 4 | 8.5 |
| | Mouth ulceration | | | | 1 | 1 | 2 | 4.3 |
| | Nausea | | 1 | | 1 | 1 | 3 | 6.4 |
| | Vomiting | | | 1 | 1 | | 2 | 4.3 |
| General disorders and administration site conditions | Influenza-like illness | | | | 1 | 2 | 3 | 6.4 |
| Infections and infestations | Nasopharyngitis | | 4 | 1 | 1 | | 6 | 10.6 |
| | Perianal abscess | 1 | | | | | 1 | 2.1 |
| Injury, poisoning and procedural complications | Contusion | | | | | 1 | 1 | 2.1 |
| | Joint Injury | | | 1 | | | 1 | 2.1 |
| Musculoskeletal and connective tissue disorders | Arthralgia | | 1 | | | | 1 | 2.1 |
| | Back Pain | | | | | 1 | 1 | 2.1 |
| Nervous system disorders | Headache | 1 | 2 | 2 | 2 | 1 | 8 | 17.0 |
| Respiratory, thoracic and mediastinal disorders | Cough | | 1 | | 1 | 1 | 3 | 6.4 |
| | Nasal congestion | | | 1 | | 1 | 2 | 4.3 |
| | Pharyngolaryngeal pain | 1 | 2 | 1 | 2 | 1 | 7 | 14.9 |
| Skin and subcutaneous tissue disorders | Rash generalised | | | | | 1 | 1 | 2.1 |

Transient redness and swelling was observed at the site of administration in some subjects, with redness affecting all subjects in cohorts 3 and 4. Although the incidence of injection site reactions appears to be increased in higher dose groups it is believed that this is related to the increased volume (and number) of injections.

Forty-eight (48) treatment emergent adverse events were reported in the seven weeks following dosing. The majority of these (44 events, 91.7%) were mild, with the remainder being moderate (4 events, 8.3%). There were no severe adverse events and no serious adverse events during this period. There was no apparent relationship between the doses of TACI-Fc5 administered and the incidence, intensity or assigned relationship of adverse events. The adverse events reported to date are summarized in Table 3.

TACI-Fc5 is believed to have shown good tolerability at doses up to 630 mg with no significant safety concerns being raised. These data support the intended doses of the proposed subject studies.

A non-compartmental analysis of TACI serum concentrations was performed. This preliminary analysis was performed using nominal sampling times. Subjects 2, 6 and 13 had measurable concentrations pre-dose, thus baseline concentrations were subtracted from all post-dose measurements prior to analysis. Pharmacokinetic parameters following single subcutaneous doses of 2.1, 70, 210 and 630 mg are summarized in Table 4. Drug concentrations were close to the limit of quantitation of the assay following the 2.1 mg dose of TACI-Fc5, limiting the value of the data at this dose level. At doses of 70 mg and above, $T_{max}$ (time to maximal absorption) ranged from 16 to 36 hours and the overall median $t_{1/2}$ (calculated from the terminal portion of the curve) was 303 hours. In addition, the AUC (extrapolated to infinity) and the $C_{max}$ increased in a greater than dose proportional manner.

TABLE 4

PK parameters

| Parameter | Treatment | n | | | Min | Median | Max | CV |
|---|---|---|---|---|---|---|---|---|
| Cmax (µg/mL) | 2.1 mg | 5 | 0.015 | 0.011 | 0.005 | 0.013 | 0.032 | 74 |
| Tmax (h) | 2.1 mg | 5 | — | — | 8 | 72 | 336 | — |
| t1/2 (h) | 2.1 mg | 4 | 204 | 180 | 45 | 203 | 365 | 88 |
| AUC(h·µg/mL) | 2.1 mg | 4 | 8.55 | 9.65 | 0.524 | 6.62 | 20.4 | 113 |
| % AUC extrap | 2.1 mg | 4 | 36 | 24 | 13 | 32 | 69 | 65 |
| CL/F (L/h) | 2.1 mg | 4 | 1.70 | 1.90 | 0.10 | 1.34 | 4.01 | 112 |
| Cmax (µg/mL) | 70 mg | 5 | 0.617 | 0.236 | 0.426 | 0.496 | 0.985 | 38 |
| Tmax (h) | 70 mg | 5 | — | — | 16 | 16 | 36 | — |
| t1/2 (h) | 70 mg | 5 | 255 | 23 | 219 | 264 | 276 | 9 |
| AUC (h · µg/mL) | 70 mg | 5 | 79.7 | 15.7 | 65.4 | 72.5 | 101 | 20 |
| % AUC extrap | 70 mg | 5 | 10 | 1 | 9 | 11 | 11 | 12 |
| CL/F (L/h) | 70 | 5 | 0.90 | 0.17 | 0.69 | 0.97 | 1.07 | 18 |
| Cmax (µg/mL) | 210 mg | 5 | 3 | 0.902 | 1.84 | 2.90 | 4.16 | 30 |
| Tmax (h) | 210 mg | 5 | — | — | 12 | 16 | 36 | — |
| t1/2 (h) | 210 mg | 5 | 429 | 160 | 169 | 433 | 568 | 37 |
| AUC (h · µg/mL) | 210 mg | 5 | 260 | 72 | 167 | 267 | 344 | 28 |
| % AUC extrap | 210 mg | 5 | 6 | 3 | 1 | 6 | 9 | 54 |
| CL/F (L&L) | 210 mg | 5 | 0.86 | 0.26 | 0.61 | 0.79 | 1.25 | 31 |
| Cmax (µg/mL) | 630 mg | 4 | 13.9 | 2.79 | 11.4 | 13.7 | 16.7 | 20 |
| Tmax (h) | 630 mg | 4 | — | — | 16 | 16 | 16 | — |
| t1/2 (h) | 630 mg | 4 | 313 | 16 | 291 | 316 | 329 | 5 |
| AUC (h · µg/mL) | 630 mg | 4 | 992 | 194 | 719 | 1040 | 1170 | 20 |
| % AUC extrap | 630 mg | 4 | 2 | 0 | 1 | 2 | 2 | 18 |
| CL/F (L/h) | 630 mg | 4 | 0.66 | 0.15 | 0.54 | 0.61 | 0.88 | 23 |

Pharmacodynamic analyses have shown reductions in baseline IgM levels in the seven weeks following single doses of 70, 210 or 630 mg. Although no clear dose response relationship could be established with the small sample size, the extent of the IgM reduction was greatest in the highest dose group. Subjects in the 70 mg dose group appeared to show a return of IgM levels towards baseline by seven weeks post dose. Levels in the higher dose groups remained suppressed at this time point. There were no apparent effects upon IgG levels, or upon the lymphocyte subpopulations that were measured by FACS.

There was increase in levels of BLyS/TACI-Fc5 complexes proportionately during the sampling period, reaching a plateau by approximately 600 hours post dose. Conclusion: human data obtained in healthy male volunteers have shown TACI-Fc5 is safe and well tolerated by subjects at doses up to 630 mg. The nature, incidence and severity of adverse events were comparable between TACI-Fc5 treatment groups and placebo. There were no clinically significant changes in physical examination findings, vital signs, 12-lead ECGs or in safety laboratory parameters. Local tolerability at the site of administration was good. These data support the proposed doses in subjects with BCM.

After single doses in healthy male subjects, TACI-Fc5 reached $T_{max}$ between 16 and 20 hours AUC increased in a dose-proportional manner, though increases in $C_{max}$ were greater than dose proportional. Median half-life of TACI-Fc5 was approximately 300 hours. A pharmacodynamic effect was noted upon IgM levels at doses of 70, 210 and 630 mg. There was no apparent effect of treatment upon IgG or lymphocyte subpopulations following a single dose of TACI-Fc5. There are no known or anticipated risks of particular severity or seriousness that have not already been taken into account in the proposed study protocols.

EXAMPLE 3

Treating RA Patients with TACI-Fc5 Compositions

RA patients are clinically assessed prior to administration of TACI-Fc5. Baseline assessments are defined as those assessments conducted immediately prior to the first administration of TACI-Fc5. The first day of TACI-Fc5 administration is designated as "Day 1". The following procedures are completed before administering to a patient the first dose of TACI-Fc5 medication: ECG; vital sign (VS) measurement; physical examination; assessment of disease activity (see Example 6); measurement of height and weight (first dose and follow up visit only); routine laboratory tests (see Table 5); calculation of urine hydroxypyridinoline/lysylpyridinoline (HP/LP) ratio; pharmacokinetic (PK) and pharmacodynamic (PD) measurement of free and total TACI-Fc5 serum concentration, serum levels of free APRIL and BlyS, BLyS/TACI-Fc5 complex, cell counts by flow cytometry and measurement of anti TACI antibodies (first dose only); and measurement of biomarkers in blood including lymphocyte subsets (blood split into three tubes and phenotyped by FACS analysis according to Table 6), IgA, IgM, IgG (including sub-typing), anti-citrullinated peptides auto-antibodies, rheumatoid factors (IgA-RF, IgM-RF, IgG-RF), C-reactive protein (CRP), TNF-α, IFN-γ, IL-6, IL-1, IL-12, and IL-8. In a subset of patients arthroscopically guided synovial biopsy or synovial fluid sampling by needle puncture is performed and PK, PD and biomarker assessments are performed in the synovial fluid. In repeat dose cohorts, many or all of these measurements are performed immediately prior to subsequent administrations of TACI-Fc5.

TABLE 5

Routine Laboratory Parameters

Blood chemistry

γ Glutamyl Transferase
Alanine Transaminase
Albumin
Alkaline Phosphatase
Aspartate Transaminase
Bilirubin - Direct (only if Total Bilirubin is outside the normal range)
Bilirubin - Total
Calcium TABLE 5-continued Routine Laboratory Parameters Creatinine
Glucose (fasting)
Inorganic Phosphorus
Potassium
Protein - Total
Electrophoresis of proteins
Complement 3
Sodium
Triglycerides[1]
Cholesterol
Urea
Uric Acid
Haematology Haematocrit
Haemoglobin
Mean Cell Haemoglobin
MCHC
Mean Cell Volume
Platelet count
Red Blood Cell count
White Blood Cell count[2]
ESR (Erythrocyte sedimentation rate)
Urinalysis pH
Leukocytes
Nitrite
Glucose
Ketones
Protein[3]
Blood[3]
Coagulation Activated Partial Thromboplastin Time
Prothrombin Time

[1]Patients shall be fasted for around 10 hours before triglyceride determination.
[2]White blood cell count shall include differential white blood cell count.
[3]If protein, blood or white cells (RBC or WBC) are present, a microscopic examination of the specimen will be performed

TABLE 6

Lymphocyte Subsets

| Tube | Antigen Markers | | | |
|------|------|------|------|------|
| Tube 1. | CD45 | CD3 | CD4 | CD8 |
| Tube 2. | CD19 | msIgG | msIgG | msIgG (control) |
| Tube 3. | CD19 | CD38 | CD27 | IgD |

Tube 1
% and Abs CD45+/CD3+ (Total T-cells)
% and Abs CD45+/CD3+/CD4+/CD8− (T-helper cells)
% and Abs CD45+/CD3+/CD4−/CD8+ (T-cytotoxic/suppressor cells)
Tube 3: Abs backcalculated using Total B cell counts (CD19+)
% and Abs CD19+ (pan B-cells)
% and Abs CD19+/IgD−/CD27− (Immature B-cell)  } Naïve
% and Abs CD19+/IgD+/CD27− (Mature B-cell)    } B cells
% and Abs CD19+/CD27+/CD38− (Memory B cell)
% and Abs CD19+/CD27+/CD38+ (Ig Secreting cells)

Approximately six hours post-dose, except for cohort 6, the following assessments are made: ECG; VS; and PK and PD sampling (only for single-dose cohorts).

The treatment with TACI-Fc5 follows a sequential dose-escalation cohort design outlined in FIG. 1. The first cohort receives a single 70 mg dose of TACI-Fc5 on Day 1. Subsequent cohorts receive doses based upon the dose-escalation algorithm, up to a maximal dose of 2940 mg. The second cohort receives three 70 mg doses of TACI-Fc5 during a one month period. The third cohort receives a single 210 mg dose of TACI-Fc5. The fourth cohort receives three 210 mg doses of TACI-Fc5 during a one month period. The fifth cohort receives a single 630 mg dose of TACI-Fc5. The sixth cohort receives seven 420 mg doses of TACI-Fc5 during a three month period.

Post-dose assessments, including collection of PK, PD and biomarker samples and safety and disease activity assessments, are completed from all cohorts at pre-defined intervals up to 14 weeks following dosing (single dose cohorts), up to 18 weeks following dosing (repeat dose cohorts 2 and 4) and up to 26 weeks following dosing (repeat dose cohort 6). Table 7 describes the post-dose assessment schedule, beginning on Day 2, of cohorts 1, 3 and 5 (the single dose cohorts). Table 8 describes the post-dose assessment schedule, starting with the first day after the final dose (Day 30) of cohorts 2 and 4. Table 9 describes the post-dose assessment schedule, starting on the day of administration of the second dose (Day 15) of cohort 6. Injection site reactions, adverse events and concomitant medications and procedures are measured throughout the study for all cohorts. Adverse event data is obtained at scheduled or unscheduled study visits following physical examination, based on information spontaneously provided by the patient and through questioning of the patient.

An adverse event is defined as any untoward medical occurrence in the form of signs, symptoms, abnormal laboratory findings, or diseases that emerge or worsen relative to baseline (i.e. the initial visit), regardless of causal relationship and even if no investigational product has been administered. The severity of an adverse event may be evaluated using the following definitions: (1) mild—the patient is aware of the event or symptom, but the event or symptom is easily tolerated; (2) moderate—the patient experiences sufficient discomfort to interfere with or reduce his or her usual level of activity; (3) severe—significant impairment of functioning wherein the patient is unable to carry out usual activities; and (4) very severe—the patient's life is at risk from the event. The relationship of the adverse event to the administration of TACI-Fc5 may be evaluated using the following definitions: (1) probable—a causal relationship is clinically/biologically highly plausible and there is a plausible time sequence between the onset of the adverse effect and administration of TACI-Fc5; (2) possible—a causal relationship is clinically/biologically plausible and there is a plausible time sequence between onset of the adverse effect and administration of TACI-Fc5; (3) unlikely—a causal relationship is improbable and another documented cause of the adverse effect is most plausible; and (4) unrelated—a causal relationship can be definitively excluded and another documented cause of the adverse effect is most plausible. Medical conditions present at baseline that do not worsen in severity or frequency during the administration of TACI-Fc5 are not considered adverse events. Exacerbation of RA is captured as part of the disease assessment and is not considered an adverse event unless possibly or probably related to the administration of TACI-Fc5.

TABLE 7

Post-dose Assessment Schedule of Cohorts 1, 3 and 5

| | D2 | D3-5 | D8 | D15 | D29 | D43 | D57 | D71 | D85-92 |
|---|---|---|---|---|---|---|---|---|---|
| ECG | X | | X | X | X | | | | X |
| VS | X | X | X | X | X | X | X | | X |
| Phys. Ex. | | | | | | | | | X |
| Phys. Ex.[A] | X | | X | X | X | X | X | | |
| ADA[B] | | | | X | X | | X | | X |
| VIS[C] | | | | | | | | | X |
| Routine Lab | X | | X | X | X | X | X | | X |
| ESR | | | | X | X | | X | | X |
| Urine HP/LP | | | | X | X | | X | | X |
| Anti-TACI-Fc5 antibody | | | | | | | | | X |
| PK/PD | X | X | X | X | X | X | X | X | X |
| Biomarkers | | X | | X | X | X | X | X | X |
| B cell counts (FACS) | | X | | X | X | X | X | X | X |
| Needle puncture | | | | | X | | | | |
| Synovial biopsy | | | | | | | X | | |

[A]complaint directed physical exam
[B]ADA = assessment of disease activity measured by CRP in serum, ESR and urinary HP/LP ratio
[C]VIS = vaccine immunization status

TABLE 8

Post-dose Assessment Schedule of Cohorts 2 and 4

| | D30 | D33 | D36 | D43 | D57 | D71 | D85 | D99 | D113-119 |
|---|---|---|---|---|---|---|---|---|---|
| ECG | | | | X | X | | | | X |
| VS | | | | X | X | X | | X | X |
| Phys. Ex. | | | | | | | | | X |
| Phys. Ex.[A] | | | | X | X | X | | X | |
| ADA[B] | | | | | X | | | | X |
| VIS[C] | | | | | | | | | X |
| Routine Lab | | | | X | X | X | | X | X |
| ESR | | | | | X | | X | | X |
| Urine HP/LP | | | | | X | | X | | X |
| Anti-TACI-Fc5 antibody | | | | | | | | | X |
| PK/PD | X | X | X | X | X | X | X | X | X |
| Biomarkers | X | X | X | X | X | X | X | X | X |
| B cell counts (FACS) | | | | X | X | X | X | X | X |
| Synovial biopsy | | | | | X | | | | |

[A]complaint directed physical exam
[B]ADA = assessment of disease activity measured by CRP in serum, ESR and urinary HP/LP ratio
[C]VIS = vaccine immunization status

TABLE 9

Post-dose Assessment Schedule of Cohort 6

| | D15 | D29 | D43 | D57 | D71 | D85 | D86 | D99 | D127 | D165-173 |
|---|---|---|---|---|---|---|---|---|---|---|
| ECG | | X | | | | | | X | | X |
| VS | X | X | X | X | X | X | X | X | X | X |
| Phys. Ex. | | | | | | | | | | X |
| Phys. Ex.[A] | X | X | X | X | X | X | X | X | X | |
| ADA[B] | X | X | | X | | X | | | X | X |
| VIS[C] | | | | | | | | | | X |
| Routine Lab | X | X | | X | | X | | | X | X |
| ESR | | | | X | | X | | | X | X |
| Urine HP/LP | X | X | | | | X | | | | X |
| Anti-TACI-Fc5 antibody | | | | | | | | | X | X |
| PK/PD | X | X | | X | | X | X | X | X | X |
| Biomarkers | X | X | | X | X | X | | | X | X |
| B cell counts (FACS) | X | X | | X | | X | | | X | X |

TABLE 9-continued

Post-dose Assessment Schedule of Cohort 6

| | D15 | D29 | D43 | D57 | D71 | D85 | D86 | D99 | D127 | D165-173 |
|---|---|---|---|---|---|---|---|---|---|---|
| Synovial biopsy | | | | | | X | | | | |
| Needle Puncture | | | | | | X | | | | |

[A]complaint directed physical exam
[B]ADA = assessment of disease activity measured by CRP in serum, ESR and urinary HP/LP ratio
[C]VIS = vaccine immunization status The dosage, administration schedule and route of administration of TACI-Fc5 are set forth in Table 10. Briefly, seventy-two male and female RA patients, aged between 18 and 70 years, are included. The patients have an established diagnosis of active, moderate to severe RA for at least 6 months, have failed not more than five DMARDs and have not used DMARDs other than methotrexate for 4 or more weeks prior to Day 1. Further, the patients are RF positive and are not pregnant during the study and until 3 months after the last administration of TACI-Fc5. These patients are divided into 6 cohorts. Three of the cohorts have 8 patients, two of the cohorts have 12 patients and one cohort has 24 patients.

TABLE 10

Dosage and Administration of TACI-Fc5

| Cohort | Drug regimen | Administration route |
|---|---|---|
| Cohort 1 (70 mg single dose, 8 patients) | TACI-Fc5 70 mg or matching placebo on Day 1 | 1 subcutaneous injection of 0.5 ml in the morning |
| Cohort 2 (3 × 70 mg repeated dose in 1 month, 12 patients) | TACI-Fc5 70 mg or matching placebo on Days 1, 15 and 29 | 1 subcutaneous injection of 0.5 ml in the morning |
| Cohort 3 (210 mg single dose, 8 patients) | TACI-Fc5 210 mg or matching placebo on Day 1 | 1 subcutaneous injection of 1.5 ml in the morning |
| Cohort 4 (3 × 210 mg repeated dose in 1 month, 12 patients) | TACI-Fc5 210 mg or matching placebo on Days 1, 15 and 29 | 1 subcutaneous injection of 1.5 ml in the morning |
| Cohort 5 (630 mg single dose, 8 patients) | TACI-Fc5 630 mg or matching placebo on Day 1 | 3 subcutaneous injection of 1.5 ml in the morning |
| Cohort 6 (7 × 420 mg repeated dose in 3 months, 24 patients) | TACI-Fc5 420 mg or matching placebo on Days 1, 15, 29, 43, 57, 71 and 85 | 2 subcutaneous injections of 1.5 ml in the morning |

EXAMPLE 4

TACI-Fc5 Injection Procedure

If subcutaneous route of administration is chosen for delivering TACI-Fc5, then the molecule is injected subcutaneously into the abdominal wall and sites rotated per the diagram below (FIG. 2). Care is taken not to inject into a blood vessel. It is extremely important to rotate sites to keep the skin healthy. Repeated injections in the same spot can cause scarring and hardening of fatty tissue. The following areas should be used for injection and rotated as follows (FIG. 2): first injection into left upper external area (FIG. 2, position 1); second injection into right lower external area (FIG. 2, position 2); third injection into left lower external area (FIG. 2, position 3); fourth injection into right upper external area (FIG. 2, position 4); and fifth injection into median lower area (FIG. 2, position 5). The aforementioned rotation scheme is repeated for additional injections.

For patients requiring more than one injection per dose, injection begins at the twelve o'clock position for the site area designated for that injection (as per FIG. 2, sites 1-5) and are then rotated sequentially clockwise, 2 hours, 4 hours, 6 hours, 8 hours and/or the 10 hour position as needed for the required number of injections per dose. Injections need to be at least 2.5 cm (1 inch) apart from each other and injected as close as possible in time. No injection of more than 1.5 mL into one injection site is allowed. If a patient experiences difficulty with injections into the abdomen, alternate areas that may be injected are anterior thighs and upper arms.

Common symptoms of site of injection reactions include itching, tenderness, warmth, and/or redness at the site of the injection.

EXAMPLE 5

Dose Escalation Protocol for Administering TACI-Ig Molecule

This dose escalation protocol for evaluation of TACI-Fc5 in RA allows for dosing of six patients in the first cohort. The first cohort receives a single dose of 70 mg, followed by 4 weeks of observation. A Safety Review Board (SRB) reviews safety data collected four weeks post-dose, and at the SRB's recommendation, the dosage is escalated to 210 mg, administered over 1 month (the second cohort) or as a single dose (the third cohort). Nine patients are dosed in the second cohort and six patients are dosed in the third cohort. The SRB then reviews safety data collected from the third cohort six weeks post-dose and at the SRB's recommendation, the dosage is escalated to 630 mg, administered over 1 month (the fourth cohort) or as a single dose (the fifth cohort). Nine patients are dosed in the fourth cohort and six patients are dosed in the fifth cohort. The SRB then reviews safety data collected from the fifth cohort six weeks post-dose and at the SRB's recommendation, cohort six receives 2940 mg over a 3 month period. Eighteen patients are dosed in the sixth cohort.

The dosages chosen are rationally based on repeated SC toxicology studies in cynomolgus monkeys and mice which indicated that TACI-Fc5 was well tolerated at 5, 20 and 80 mg/k. Apart from the effects on the immune cells that are the expected results of TACI-Fc5 pharmacodynamic activity, the only findings were a significant decrease of plasma total protein and slight subcutaneous reaction with the highest SC dose of 80 mg/kg in monkeys and a transient hyperactivity in the Irwin test in mice at the dose of 80 mg/kg. Therefore, 20 mg/kg is the highest dose not associated with adverse findings in both species.

In addition, doses of 2.1, 70, 210 and 630 mg have been administered as single subcutaneous doses to healthy volunteers. There have been no safety or tolerability concerns raised at these doses. On the basis of pre-clinical data and the preliminary findings in healthy volunteers, 70 mg has been selected as an appropriate starting dose for patients with RA.

The doses and dosing regimens foreseen in the RA patients in the present study ranges from 1 mg/kg to 9 mg/kg twice a month (when normalized for a 70 kg person), which fits well with the dose range studied in monkeys. Repeated administration in monkeys has shown a clear dose-response relationship.

EXAMPLE 6

Assessment of Disease Progression

Disease progression is measured by Disease Activity Score, Physician's Global Assessment of Disease Activity, Patient's Global Assessment of Disease Activity, morning stiffness and patient's assessment of pain, disease activity and physical function.

The Disease Activity Score (DAS) is a combined index that has developed to measure the disease activity in patients with RA. It has been extensively validated for its use in clinical trials in combination with the EULAR response criteria. The original DAS included the Ritchie articular index, the 44 swollen joint count, the ESR and a general health assessment on VAS. After validation of the 28 non-graded joint count for tenderness and swelling, DAS 28 has been developed including 28 joint counts. The results of DAS and DAS28 are not directly interchangeable.

Using the DAS, several thresholds have been developed for high disease activity, low disease activity or even remission. Also, response criteria have been developed based on DAS, so when the DAS of a patient is measured at two time points, the clinical response can be assessed.

Disease variables needed to calculate the DAS28 are: swollen joint count (28 joints); tender joint count (28 joints); ESR (mm after 1 hour); Patients general health (GH) or global disease activity (visual analogue scale (VAS) of 100 mm)—in this study named Patient's Global Assessment of Disease Activity. Twenty-eight tender and swollen joint scores include the following joints: shoulders, elbows, wrists, metacarpophalangeal joints, proximal interphalangeal joints and the knees.

The formula used to calculate the DAS is the following: $DAS28 = 0.56*sqrt(tender28) + 0.28*sqrt(swollen28) + 0.70*ln(ESR) + 0.014*GH$. The DAS provides a number on a scale from 0 to 10 indicating the current activity of the rheumatoid arthritis. A DAS28 above 5.1 means high disease activity and a DAS28 below 3.2 indicates low disease activity. Remission is achieved by a DAS28 lower than 2.6. Comparing the DAS28 from one patient on two different time points, it is possible to define improvement or response.

Patient's Assessment of Pain and Patient's Global Assessment of Disease Activity are assessed using a horizontal visual analogue scale (VAS).

The Physician's Global Assessment of Disease Activity measures the patient's current disease activity using a 5 point graded scale (Likert scale) where 0=asymptomatic, 1=mild, 2=moderate, 3=severe and 4=very severe.

The Patient's Assessment of Physical Function is measured based on the patient's response to a Health Assessment Questionnaire (HAQ) which queries the patient regarding the patient's ability over the previous week to perform everyday tasks such as dressing and grooming, eating, walking, and whether the patient required aids or equipment to perform any of the aforementioned tasks.

The presence of morning stiffness is assessed by interviewing the patient and if present, the duration is recorded.

---

What is claimed is:

1. A method for treatment of rheumatoid arthritis in a human patient comprising administering to the patient a composition comprising a fusion molecule selected from the group consisting of:
   (a) a fusion molecule comprising
      (i) TACI extracellular domain wherein said TACI extracellular domain is at least 95% identical to SEQ ID NO:1 and binds BlyS; and
      (ii) a human immunoglobulin-constant domain;
   (b) a fusion molecule comprising amino acids 30-110 of SEQ ID NO: 1 and a human immunoglobulin-constant domain;
   (c) a fusion molecule consisting of amino acids 30-110 of SEQ ID NO: 1 and a human immunoglobulin-constant domain;
   (d) a fusion molecule consisting of SEQ ID NO: 2; and
   (e) a fusion molecule consisting of amino acids 30-110 of SEQ ID NO:1 and the human immunoglobulin-constant domain of SEQ ID NO: 2;
   wherein said composition is administered in an amount from 1.0 mg per 1 kg of patient's body weight to 9.0 mg per 1 kg of patient's body weight and wherein said composition is administered in said amount 7 times during a twelve-week interval, 3 times during a four-week interval or every other week for 2 to 30 weeks.

2. The method of claim 1, wherein said composition is administered in said amount 7 times during a twelve-week interval.

3. The method of claim 2, wherein said composition is administered in said amount 7 times during a twelve-week interval, followed by additional administrations of said composition at said amount.

4. The method of claim 1, said composition is administered in said amount 3 times during a four-week interval.

5. The method of claim 4, wherein said composition is administered in said amount 3 times during a four-week interval, followed by additional administrations of said composition at said amount.

6. The method of claim 1, wherein said composition is administered in said amount every other week for 2 to 30 weeks.

7. The method of claim 1, wherein said method further comprises co-administering to the patient a second medicament.

8. The method of claim 7, wherein said second medicament is selected from the group consisting of: hydroxychloroquine, sulfasalazine, methotrexate, leflunomide, rituximab, infliximab, azathioprine, D-penicillamine, Gold (oral or intramuscular), minocycline, cyclosporine, a corticosteroid, a non-steroidal anti-inflammatory drug (NSAIDS), a cytokine, an anti-cytokine and an interferon.

9. The method of claim 1, wherein said composition is administered subcutaneously, orally or intravenously.

10. The method of claim 1, wherein said human immunoglobulin-constant domain is a human immunoglobulin-constant domain of IgG.

11. The method of claim 10, wherein said human immunoglobulin-constant domain comprises Fc5.

12. A method for treatment of rheumatoid arthritis in a human patient comprising administering to the patient a composition comprising a fusion molecule selected from the group consisting of:
   (a) a fusion molecule comprising amino acids 30-110 of SEQ ID NO: 1 and a human immunoglobulin-constant domain;
   (b) a fusion molecule consisting of amino acids 30-110 of SEQ ID NO: 1 and a human immunoglobulin-constant domain; and
   (c) a fusion molecule consisting of SEQ ID NO: 2;
   wherein said composition is administered in an amount from 1.0 mg per 1 kg of patient's body weight to 9.0 mg per 1 kg of patient's body weight and wherein said composition is administered in said amount 7 times during a twelve-week interval, 3 times during a four-week interval or every other week for 2 to 30 weeks.

13. The method of claim 12, said method further comprising co-administering to the patient a second medicament.

14. The method of claim 13, wherein said second medicament is selected from the group consisting of: hydroxychloroquine, sulfasalazine, methotrexate, leflunomide, rituximab, infliximab, azathioprine, D-penicillamine, Gold (oral or intramuscular), minocycline, cyclosporine, a corticosteroid, a non-steroidal anti-inflammatory drug (NSAIDS), a cytokine, an anti-cytokine and an interferon.

15. The method of claim 12, wherein said composition is administered subcutaneously, orally or intravenously.

16. The method of claim 12, wherein said human immunoglobulin-constant domain is a human immunoglobulin-constant domain of IgG.

17. The method of claim 15, wherein said human immunoglobulin-constant domain comprises Fc5.

* * * * *

SEQUENCE LISTING

<160> NUMBER OF SEQ ID NOS: 2

<210> SEQ ID NO 1
<211> LENGTH: 154
<212> TYPE: PRT
<213> ORGANISM: Artificial
<220> FEATURE:
<223> OTHER INFORMATION: Amino acids 1-154 of the extracellular domain of TACI.

<400> SEQUENCE: 1

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys
145                 150

<210> SEQ ID NO 2
<211> LENGTH: 348
<212> TYPE: PRT
<213> ORGANISM: Homo Sapien

<400> SEQUENCE: 2

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser

```
                290                 295                 300
Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
                340                 345
```